(12) United States Patent
Byrd et al.

(10) Patent No.: US 11,717,337 B2
(45) Date of Patent: Aug. 8, 2023

(54) ELECTROPORATION SYSTEMS AND CATHETERS FOR ELECTROPORATION SYSTEMS

(71) Applicant: ST. JUDE MEDICAL, CARDIOLOGY DIVISION, INC., St. Paul, MN (US)

(72) Inventors: Israel Byrd, Richfield, MN (US); Jeffrey M. Fish, Maple Grove, MN (US); Jeffrey A. Schweitzer, St. Paul, MN (US); Daniel J. Potter, Stillwater, MN (US); Gregory K. Olson, Elk River, MN (US); Frederik H. M. Wittkampf, Lage Vuursche (NL); Rene Van Es, Utrecht (NL)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 700 days.

(21) Appl. No.: 16/464,738

(22) PCT Filed: Nov. 29, 2017

(86) PCT No.: PCT/US2017/063650
§ 371 (c)(1),
(2) Date: May 29, 2019

(87) PCT Pub. No.: WO2018/102376
PCT Pub. Date: Jun. 7, 2018

(65) Prior Publication Data
US 2019/0307500 A1    Oct. 10, 2019

Related U.S. Application Data

(60) Provisional application No. 62/431,735, filed on Dec. 8, 2016, provisional application No. 62/427,195, filed
(Continued)

(51) Int. Cl.
  *A61B 18/12*    (2006.01)
  *A61B 18/14*    (2006.01)
  (Continued)

(52) U.S. Cl.
  CPC ...... *A61B 18/1233* (2013.01); *A61B 18/1492* (2013.01); *A61B 34/20* (2016.02);
  (Continued)

(58) Field of Classification Search
  CPC . A61B 18/1233; A61B 18/1492; A61B 34/20; A61B 5/287; A61B 2018/00351;
  (Continued)

(56) References Cited

U.S. PATENT DOCUMENTS 4,248,231 A * 2/1981 Herczog ............... A61B 18/14
                                                      606/48
4,727,874 A * 3/1988 Bowers ............... A61B 18/1206
                                                      606/38

(Continued)

FOREIGN PATENT DOCUMENTS

EP    0358336 A1 *  3/1990  ......... A61B 18/1206
EP    0787019 A1     8/1997
(Continued)

OTHER PUBLICATIONS

International Search Report and Written Opinion for International Application No. PCT/US2017/063650, dated Feb. 5, 2018, 12 pages.

*Primary Examiner* — Khadijeh A Vahdat
*Assistant Examiner* — Marina Delaney Templeton
(74) *Attorney, Agent, or Firm* — Armstrong Teasdale LLP

(57) ABSTRACT

The present disclosure provides electroporation systems, methods of controlling electroporation systems to limit electroporation arcs through intracardiac catheters, and catheters for electroporation systems. One method of controlling
(Continued)

an electroporation system including a direct current (DC) energy source, a return electrode connected to the DC energy source, and a catheter connected to the DC energy source is disclosed. The catheter has a at least one catheter electrode. The method includes positioning the return electrode near a target location within a body and positioning the catheter electrode adjacent the target location within the body. A system impedance is determined with the return electrode positioned near the target location and the catheter electrode positioned within the body. The system impedance is adjusted to a target impedance to arcing from the catheter electrode.

8 Claims, 19 Drawing Sheets

Related U.S. Application Data on Nov. 29, 2016, provisional application No. 62/427,190, filed on Nov. 29, 2016.

(51) Int. Cl.
*A61B 34/20* (2016.01)
*A61B 18/00* (2006.01)
*A61B 18/16* (2006.01)
*A61B 5/287* (2021.01)

(52) U.S. Cl.
CPC ..... *A61B 5/287* (2021.01); *A61B 2018/00351* (2013.01); *A61B 2018/00375* (2013.01); *A61B 2018/00577* (2013.01); *A61B 2018/00613* (2013.01); *A61B 2018/00755* (2013.01); *A61B 2018/00839* (2013.01); *A61B 2018/00875* (2013.01); *A61B 2018/1266* (2013.01); *A61B 2018/1407* (2013.01); *A61B 2018/1435* (2013.01); *A61B 2018/167* (2013.01); *A61B 2034/2051* (2016.02); *A61B 2034/2053* (2016.02)

(58) Field of Classification Search
CPC ........... A61B 2018/00375; A61B 2018/00577; A61B 2018/00613; A61B 2018/00755; A61B 2018/00839; A61B 2018/00875; A61B 2018/1266; A61B 2018/1407; A61B 2018/1435; A61B 2018/167; A61B 2034/2051; A61B 2034/2053; A61B 2018/00666; A61B 2018/00779; A61N 1/327
See application file for complete search history.

(56) References Cited

U.S. PATENT DOCUMENTS

| | | | | |
|---|---|---|---|---|
| 4,896,671 A * | 1/1990 | Cunningham | ..... | A61B 18/1492 600/374 |
| 5,300,068 A * | 4/1994 | Rosar | ..... | A61B 18/1492 606/32 |
| 5,370,645 A * | 12/1994 | Klicek | ..... | A61B 18/1206 606/35 |
| 5,628,745 A * | 5/1997 | Bek | ..... | A61B 18/1206 606/38 |
| 5,759,158 A * | 6/1998 | Swanson | ..... | A61B 5/287 600/508 |
| 5,772,659 A * | 6/1998 | Becker | ..... | A61B 18/1206 322/7 |
| 5,797,903 A * | 8/1998 | Swanson | ..... | A61L 29/085 600/374 |
| 5,837,001 A * | 11/1998 | Mackey | ..... | A61B 18/1206 607/102 |
| 6,004,319 A * | 12/1999 | Goble | ..... | A61B 18/1206 606/48 |
| 6,019,757 A * | 2/2000 | Scheldrup | ..... | A61B 18/1492 606/49 |
| 6,023,638 A * | 2/2000 | Swanson | ..... | A61B 5/6858 600/510 |
| 6,090,106 A * | 7/2000 | Goble | ..... | A61B 18/1206 606/41 |
| 6,107,699 A * | 8/2000 | Swanson | ..... | A61B 18/1492 307/112 |
| 6,149,620 A * | 11/2000 | Baker | ..... | A61B 18/1402 604/22 |
| 6,162,216 A * | 12/2000 | Guziak | ..... | A61B 18/1482 606/42 |
| 6,409,722 B1 * | 6/2002 | Hoey | ..... | A61B 18/1206 606/34 |
| 6,428,537 B1 * | 8/2002 | Swanson | ..... | A61B 18/1492 606/41 |
| 6,464,696 B1 * | 10/2002 | Oyama | ..... | A61B 18/149 606/34 |
| 6,678,558 B1 * | 1/2004 | Dimmer | ..... | A61N 1/327 607/3 |
| 6,936,024 B1 * | 8/2005 | Houser | ..... | A61B 18/1492 604/22 |
| 7,054,685 B2 * | 5/2006 | Dimmer | ..... | A61N 1/325 607/3 |
| 7,263,397 B2 | 8/2007 | Hauck et al. | | |
| 7,553,309 B2 * | 6/2009 | Buysse | ..... | A61B 18/1206 606/34 |
| 7,620,451 B2 * | 11/2009 | Demarais | ..... | A61N 1/05 607/3 |
| 8,048,067 B2 * | 11/2011 | Davalos | ..... | A61B 18/1233 606/32 |
| 8,114,070 B2 * | 2/2012 | Rubinsky | ..... | A61N 1/327 606/32 |
| 8,221,411 B2 * | 7/2012 | Francischelli | ..... | A61B 18/1442 606/41 |
| 8,251,986 B2 * | 8/2012 | Chornenky | ..... | A61B 18/14 606/32 |
| 8,282,631 B2 * | 10/2012 | Davalos | ..... | A61B 18/1233 606/32 |
| 9,211,155 B2 * | 12/2015 | Fruland | ..... | A61B 34/25 |
| 9,283,051 B2 | 3/2016 | Garcia et al. | | |
| 9,308,043 B2 * | 4/2016 | Zarins | ..... | A61N 1/327 |
| 9,414,881 B2 * | 8/2016 | Callas | ..... | A61B 18/14 |
| 9,468,497 B2 * | 10/2016 | Zarins | ..... | A61B 5/4848 |
| 9,649,148 B2 * | 5/2017 | Woloszko | ..... | A61B 18/042 |
| 10,188,449 B2 | 1/2019 | Gilbert | | |
| 10,238,447 B2 * | 3/2019 | Neal, II | ..... | A61B 34/10 |
| 10,271,893 B2 | 4/2019 | Stewart et al. | | |
| 10,342,600 B2 | 7/2019 | Callas et al. | | |
| 10,470,822 B2 | 11/2019 | Garcia et al. | | |
| 10,531,914 B2 | 1/2020 | Stewart et al. | | |
| 2002/0052599 A1 * | 5/2002 | Goble | ..... | A61B 18/1445 606/40 |
| 2002/0058933 A1 * | 5/2002 | Christopherson | ..... | A61B 18/14 606/41 |
| 2002/0087208 A1 * | 7/2002 | Koblish | ..... | A61B 18/1492 607/113 |
| 2002/0095151 A1 * | 7/2002 | Dahla | ..... | A61B 18/148 606/41 |
| 2002/0193833 A1 * | 12/2002 | Dimmer | ..... | A61N 1/325 607/3 |
| 2003/0028189 A1 * | 2/2003 | Woloszko | ..... | A61B 18/14 606/45 |
| 2003/0187430 A1 * | 10/2003 | Vorisek | ..... | A61B 18/14 606/34 |
| 2004/0054366 A1 * | 3/2004 | Davison | ..... | A61B 18/14 606/39 |
| 2004/0167508 A1 * | 8/2004 | Wham | ..... | A61B 18/1445 606/32 |
| 2004/0230189 A1 * | 11/2004 | Keppel | ..... | A61B 18/1206 606/34 |
| 2004/0236376 A1 | 11/2004 | Miklavcic et al. | | |

(56) References Cited

U.S. PATENT DOCUMENTS

| | | | |
|---|---|---|---|
| 2005/0070896 A1* | 3/2005 | Daniel | A61B 18/1477 606/50 |
| 2005/0159745 A1* | 7/2005 | Truckai | A61B 18/1442 606/51 |
| 2005/0171523 A1* | 8/2005 | Rubinsky | A61B 18/12 606/34 |
| 2005/0171574 A1* | 8/2005 | Rubinsky | A61N 1/0412 607/2 |
| 2006/0041277 A1* | 2/2006 | Deem | A61N 1/36128 607/3 |
| 2006/0224192 A1* | 10/2006 | Dimmer | A61N 1/325 607/3 |
| 2007/0043345 A1* | 2/2007 | Davalos | A61B 18/1233 606/32 |
| 2007/0179490 A1* | 8/2007 | Azar | A61B 18/10 606/28 |
| 2007/0250052 A1* | 10/2007 | Wham | A61B 18/1206 606/34 |
| 2008/0077129 A1* | 3/2008 | Van Wyk | A61B 18/149 606/46 |
| 2008/0114351 A1* | 5/2008 | Irisawa | A61B 18/1206 606/41 |
| 2008/0132884 A1* | 6/2008 | Rubinsky | A61N 1/327 606/34 |
| 2008/0132885 A1 | 6/2008 | Rubinsky et al. | |
| 2008/0255642 A1* | 10/2008 | Zarins | A61F 7/12 607/99 |
| 2009/0082765 A1* | 3/2009 | Collins | A61B 18/18 606/38 |
| 2009/0281477 A1* | 11/2009 | Mikus | A61B 18/1477 604/21 |
| 2010/0016848 A1* | 1/2010 | Desai | A61B 18/1492 606/33 |
| 2010/0094275 A1* | 4/2010 | Wham | A61B 18/1206 606/33 |
| 2010/0241116 A1* | 9/2010 | Benamou | A61B 18/1206 606/33 |
| 2010/0261994 A1* | 10/2010 | Davalos | A61N 1/0412 600/411 |
| 2011/0112520 A1* | 5/2011 | Michael | A61N 1/0412 606/13 |
| 2011/0160514 A1* | 6/2011 | Long | A61B 18/16 600/2 |
| 2012/0083779 A1* | 4/2012 | Hosier | A61B 18/1233 606/33 |
| 2012/0098351 A1* | 4/2012 | Ross | A61B 18/1233 307/104 |
| 2012/0116288 A1 | 5/2012 | Miklavcic et al. | |
| 2012/0220997 A1* | 8/2012 | Johnston | A61B 18/1206 606/40 |
| 2012/0277741 A1* | 11/2012 | Davalos | A61B 18/1233 606/41 |
| 2012/0310237 A1* | 12/2012 | Swanson | A61B 18/08 606/41 |
| 2013/0030430 A1 | 1/2013 | Stewart et al. | |
| 2013/0218157 A1* | 8/2013 | Callas | A61B 18/14 606/41 |
| 2013/0338467 A1* | 12/2013 | Grasse | A61B 18/1492 600/373 |
| 2014/0005667 A1* | 1/2014 | Stulen | A61B 18/1445 606/45 |
| 2014/0018880 A1* | 1/2014 | Zarins | A61N 1/36017 607/44 |
| 2014/0276753 A1* | 9/2014 | Wham | A61B 18/1206 606/33 |
| 2014/0303615 A1* | 10/2014 | Amoah | B03C 3/38 606/34 |
| 2015/0005758 A1* | 1/2015 | Berger | A61B 34/73 606/34 |
| 2015/0105701 A1* | 4/2015 | Mayer | A61B 18/1206 601/3 |
| 2016/0022349 A1* | 1/2016 | Woloszko | A61B 18/1206 606/34 |
| 2016/0051324 A1 | 2/2016 | Stewart et al. | |
| 2016/0058493 A1 | 3/2016 | Neal et al. | |
| 2016/0066978 A1* | 3/2016 | Keller | A61B 18/14 606/40 |
| 2016/0128767 A1* | 5/2016 | Azamian | A61B 18/1492 606/41 |
| 2016/0184003 A1* | 6/2016 | Srimathveeravalli | A61B 18/1206 606/39 |
| 2016/0213922 A1* | 7/2016 | Goldberg | A61N 1/0464 |
| 2016/0331441 A1* | 11/2016 | Konings | A61B 18/1206 |
| 2017/0035499 A1* | 2/2017 | Stewart | A61B 18/1206 |
| 2017/0246455 A1 | 8/2017 | Athos et al. | |
| 2017/0319851 A1 | 11/2017 | Athos et al. | |
| 2018/0071008 A1* | 3/2018 | Van Wyk | A61B 18/18 |
| 2018/0071014 A1* | 3/2018 | Neal | A61M 25/00 |
| 2018/0085160 A1* | 3/2018 | Viswanathan | A61B 18/1492 |
| 2018/0132922 A1* | 5/2018 | Neal, II | A61B 18/12 |
| 2018/0221078 A1 | 8/2018 | Howard et al. | |
| 2019/0030328 A1 | 1/2019 | Stewart et al. | |
| 2019/0350647 A1 | 11/2019 | Ramberg et al. | |
| 2020/0138506 A1 | 5/2020 | Fraasch et al. | |
| 2021/0121228 A1* | 4/2021 | Byrd | A61B 18/1206 |

FOREIGN PATENT DOCUMENTS

| | | |
|---|---|---|
| WO | 2014025394 A1 | 2/2014 |
| WO | 2015103530 A1 | 7/2015 |
| WO | 2015175944 A1 | 11/2015 |

\* cited by examiner

ELECTROPORATION SYSTEMS AND CATHETERS FOR ELECTROPORATION SYSTEMS

CROSS REFERENCE TO RELATED APPLICATIONS

This application is the national stage entry of PCT/US2017/063650, filed on Nov. 29, 2017, which claims the benefit of priority to U.S. provisional application Ser. No. 62/427,190, filed Nov. 29, 2016, U.S. provisional application Ser. No. 62/427,195, filed Nov. 29, 2016, and U.S. provisional application Ser. No. 62/431,735, filed Dec. 8, 2016, all of which are incorporated herein by reference in their entirety.

A. FIELD OF THE DISCLOSURE

The present disclosure relates generally to medical devices that are used in the human body. In particular, in many embodiments, the present disclosure relates to electroporation systems and methods of controlling electroporation systems to limit electroporation arcs from catheters. Further, the present disclosure relates to systems and methods for identifying such arcs.

B. BACKGROUND

It is generally known that ablation therapy may be used to treat various conditions afflicting the human anatomy. One such condition in which ablation therapy finds a particular application in, for example, is the treatment of atrial arrhythmias. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmia (i.e., irregular heart rhythm) can create a variety of dangerous conditions including loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

One candidate for use in therapy of cardiac arrhythmias is electroporation. Electroporation therapy involves electric-field induced pore formation on the cell membrane. The electric field may be induced by applying a direct current (DC) signal delivered as a relatively short duration pulse which may last, for instance, from a nanosecond to several milliseconds. Such a pulse may be repeated to form a pulse train. When such an electric field is applied to tissue in an in vivo setting, the cells in the tissue are subjected to transmembrane potential, which opens the pores on the cell wall, hence the term electroporation. Electroporation may be reversible (i.e., the temporally-opened pores will reseal) or irreversible (i.e., the pores will remain open). For example, in the field of gene therapy, reversible electroporation (i.e., temporarily open pores) is used to transfect high molecular weight therapeutic vectors into the cells. In other therapeutic applications, a suitably configured pulse train alone may be used to cause cell destruction, for instance by causing irreversible electroporation.

BRIEF SUMMARY OF THE DISCLOSURE

The present disclosure generally relates to electroporation systems, methods of controlling electroporation systems, and catheters for electroporation systems. In many embodiments, the electroporation system includes a monophasic direct current (DC) energy source connected to a catheter including several catheter electrodes. Other embodiments and descriptions of the present disclosure are set forth below.

In one embodiment, the present disclosure is directed to a method of controlling an electroporation system including a direct current (DC) energy source, a return electrode connected to the DC energy source, and a catheter connected to the DC energy source. The catheter has at least one catheter electrode. The method includes positioning the return electrode near a target location within a body and positioning the catheter electrode adjacent the target location within the body. A system impedance is determined with the return electrode positioned near the target location and the catheter electrode positioned within the body. The system impedance is adjusted to a target impedance to limit arcing from the catheter electrode.

In another embodiment, the present disclosure is directed to an electroporation system including a monophasic energy source, a return electrode, a catheter, and a variable impedance. The return electrode is connected to a return of the monophasic energy source. The catheter is connected to an output of the monophasic energy source and includes at least one catheter electrode. The variable impedance is connected to the monophasic energy source to selectively vary an impedance of the electroporation system.

In another embodiment, the present disclosure is directed to a method of controlling an electroporation system including a monophasic energy source, a return electrode connected to the monophasic energy source, and a catheter connected to the monophasic energy source. The catheter has an electrode surface area. The method includes determining a system impedance with the patch electrode on a body and the catheter positioned within the body adjacent a target area. The system impedance is adjusted to a target impedance selected to cause the monophasic energy source to produce a current density on the electrode surface area of less than 150 milliamps per square millimeter ($mA/mm^2$). For example, at least one resistor may be connected to the catheter or return electrode to adjust the system impedance. Alternatively, a pulse energy may be modified (e.g., using a knob or other input mechanism included in the electroporation system) to adjust the system impedance.

In another embodiment, the present disclosure is directed to a catheter including a handle, a shaft, a distal loop subassembly, and a plurality of electrode wires. The handle includes an insulated electrical connector at a proximal end of the handle configured for connection to an electroporation generator and defines an interior channel. The shaft is coupled to and extends from a distal end of the handle. The shaft defines an interior channel. The distal loop subassembly is coupled to a distal end of the shaft and includes a loop having a plurality of catheter electrodes disposed thereon. Each electrode wire of the plurality of electrode wires is coupled to a different catheter electrode of the plurality of catheter electrodes and extends from the distal loop assembly to the connector through the interior channels of the shaft and the handle. Each electrode wire of the plurality of electrode wires is surrounded by an insulator with a thickness of at least about 1.5 thousandths of an inch.

In another embodiment, the present disclosure is directed to a system including an electroporation subsystem having an electroporation energy source, a second subsystem configured for at least one of diagnostic, mapping, and navigation operations, a catheter and a selection interface. The catheter includes a plurality of catheter electrodes, an electrical connector, and a plurality of electrode wires. Each electrode wire of the plurality of electrode wires is coupled to a different catheter electrode of the plurality of electrodes and the electrical connector. The selection interface is coupled to the electroporation subsystem, the second subsystem, and the catheter's electrical connector. The selection interface is configured for selectively coupling the catheter to a selected one of the electroporation subsystem and the second subsystem.

In another embodiment, the present disclosure is directed to an electroporation system including a monophasic energy source, a return electrode connected to a return of the monophasic energy source, and a catheter connected to an output of the monophasic energy source. The catheter includes a handle, a shaft, a distal loop subassembly and a plurality of electrode wires. The handle includes an insulated electrical connector at a proximal end of the handle configured for connection to an electroporation generator and defines an interior channel. The shaft is coupled to and extends from a distal end of the handle. The shaft defines an interior channel. The distal loop subassembly is coupled to a distal end of the shaft and includes a loop having a plurality of catheter electrodes disposed thereon. Each electrode wire of the plurality of electrode wires is coupled to a different catheter electrode of the plurality of catheter electrodes and extends from the distal loop assembly to the connector through the interior channels of the shaft and the handle. Each electrode wire of the plurality of electrode wires is surrounded by an insulator with a thickness of at least about 1.5 thousandths of an inch.

In another embodiment, a method of detecting arcing in an electroporation system is provided. The electroporation system includes a direct current (DC) energy source, a return electrode connected to the DC energy source, and a catheter connected to the DC energy source, the catheter having at least one catheter electrode. The method includes positioning the return electrode near a target location within a body, and positioning the catheter electrode within the body adjacent the target location within the body. The method further includes monitoring a system impedance with the return electrode positioned near the target location and the catheter electrode positioned within the body, detecting a positive deflection in the system impedance, the positive deflection indicative of arcing, and generating an alert, based on the detection, the alert indicating that arcing has occurred.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure relates generally to medical devices that are used in the human body. In particular, in many embodiments, the present disclosure relates to electroporation systems and methods of controlling electroporation systems to limit electroporation arcs from catheters. In some embodiments, the catheters are intracardiac catheters. Electroporation arcs can occur from catheter electrodes to a blood pool when an insulating layer of gas covers the catheter electrode. The insulating layer of gas may be created by the electrical pulse output by an electroporation generator and the volume of gas is proportional to the energy of the pulse. The disclosed embodiments may lead to more consistent and improved patient outcomes with less chance of undesired electrical arcing. In many embodiments, the present disclosure also relates to catheters for electroporation systems. The disclosed embodiments may lead to more consistent and improved patient outcomes with less chance of undesired electrical arcing. It is contemplated, however, that the described features and methods of the present disclosure as described herein may be incorporated into any number of systems as would be appreciated by one of ordinary skill in the art based on the disclosure herein.

Figure 1:
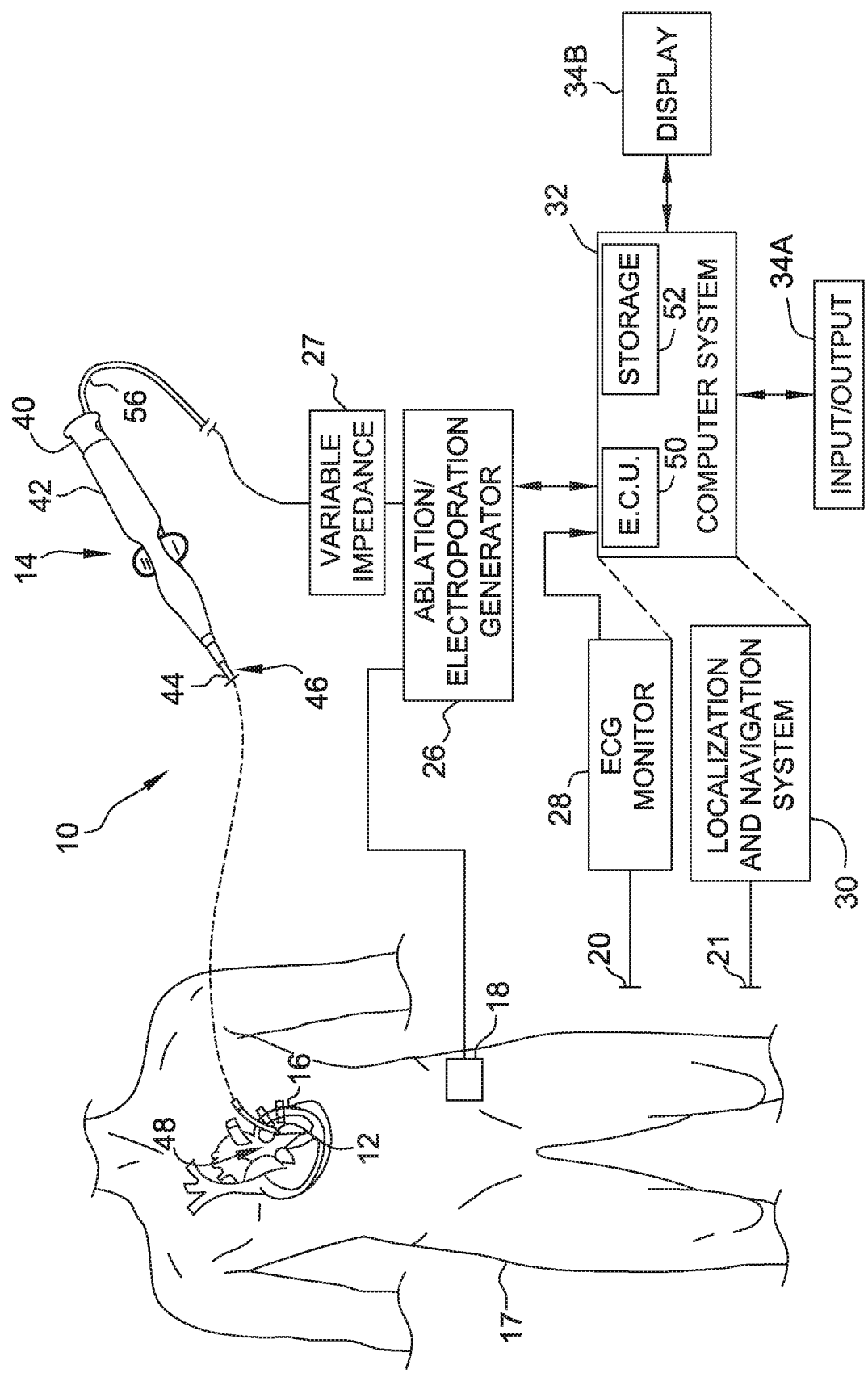
FIG. 1 is a schematic and block diagram view of a system incorporating embodiments for electroporation therapy including a variable system impedance to limit electrical arcing.

Referring now to the drawings, FIG. 1 is a diagrammatic and block diagram view of a system 10 for electroporation therapy. In general, the various embodiments include an electrode assembly disposed at the distal end of a catheter. As used herein, "proximal" refers to a direction toward the end of the catheter near the clinician and "distal" refers to a direction away from the clinician and (generally) inside the body of a patient. The electrode assembly includes one or more individual, electrically-isolated electrode elements. Each electrode element, also referred to herein as a catheter electrode, is individually wired such that it can be selectively paired or combined with any other electrode element to act as a bipolar or a multi-polar electrode.

System 10 may be used for irreversible electroporation to destroy tissue. In particular, system 10 may be used for electroporation-induced primary necrosis therapy, which refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field in the form of short-duration direct current (DC) pulses (e.g., 0.1 to 20 ms duration) between closely spaced electrodes capable of delivering an electric field strength of about 0.1 to 1.0 kV/cm. As described in greater detail below, system 10 may be used with a high output hoop catheter for high output (e.g., high voltage and/or high current) electroporation procedures.

In one embodiment, all electrodes of the hoop catheter deliver an electric current simultaneously. That is, the electrodes are electrically connected in parallel during the application. Delivering electric current simultaneously using a plurality of electrodes arranged in a circular fashion facilitates creating a sufficiently deep lesion for electroporation. To facilitate activating electrodes simultaneously, the electrodes may be switchable between being connected to a 3D mapping system and being connected to EP amplifiers.

When using a circular hoop catheter, the current density in surrounding tissue decays linearly with distance from the electrodes when all electrodes deliver an electric current simultaneously. If, however, less than all the electrodes delivery an electric current simultaneously, the current density near electrodes that do not participate in current delivery will decay exponentially, instead of linearly. The exponential decay in current may result in insufficient lesion depth, gaps in an ablation line, and undesired procedural outcomes. Accordingly, in at least some of the embodiments described herein, current is delivered simultaneously by all electrodes (e.g., even those with low or no tissue contact). Simultaneous delivery of all electrodes in a circular arrangement may also be used for other types of electrical energy. For example, for RF ablation, simultaneous delivery (i.e., with an in-phase electrical RF current) via all electrodes (instead of a phased array or sequential delivery) may result in improved outcomes.

Figure 12:
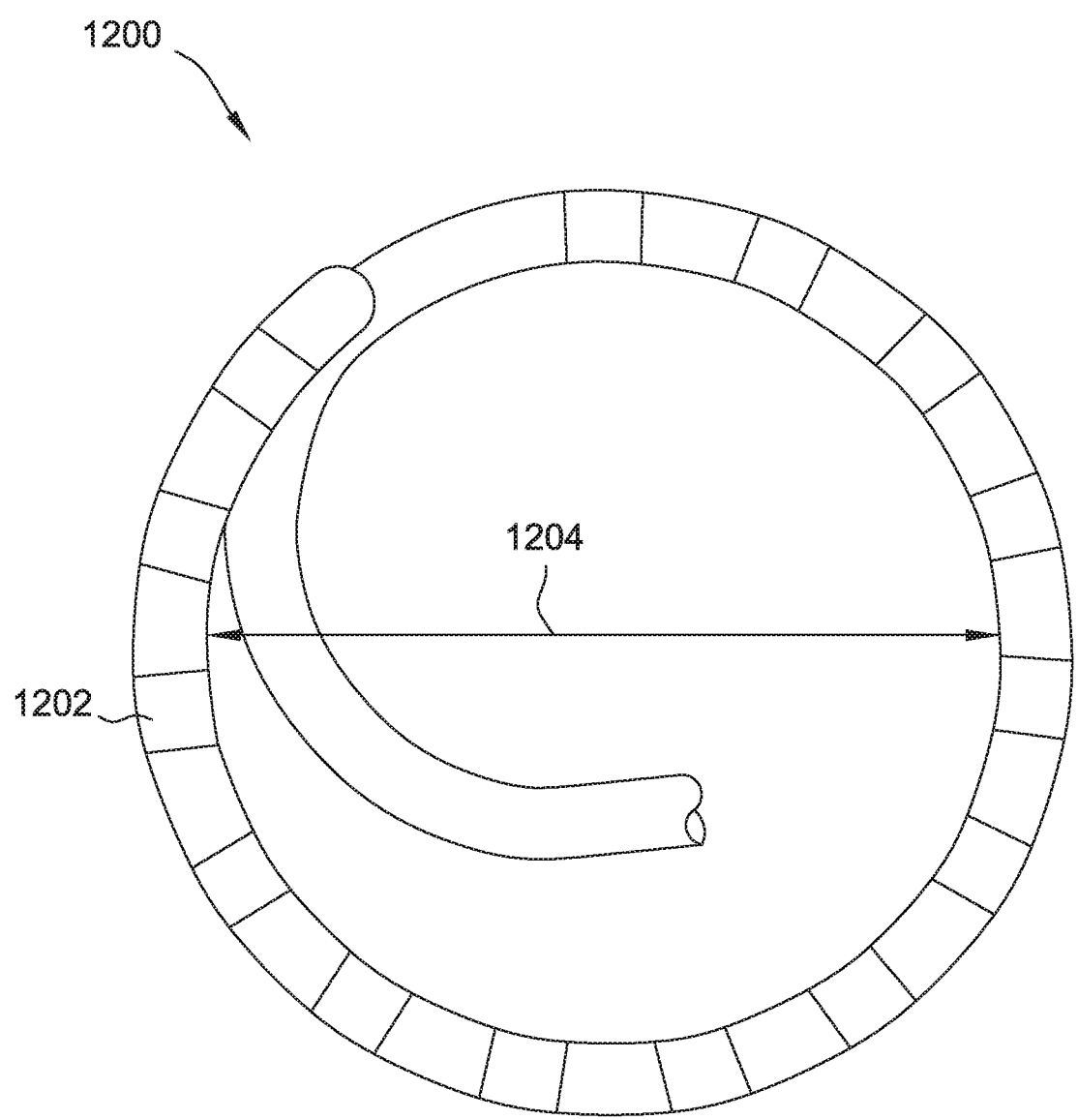
FIG. 12 is a variable diameter hoop catheter in an expanded configuration.
Figure 13:
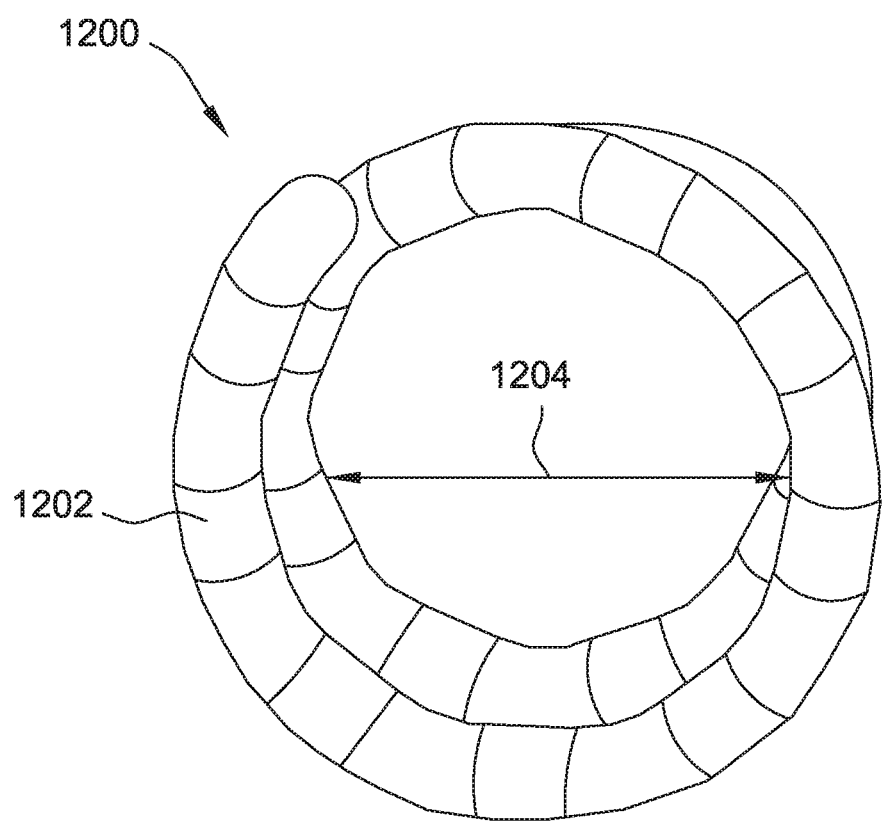
FIG. 13 is the variable diameter hoop catheter of FIG. 12 in a contracted configuration.

For a hoop catheter (e.g., as shown in FIGS. 12 and 13), when the hoop diameter is minimized, multiple electrodes will overlap, such that a subset of the electrodes form a circle by themselves (see, e.g., FIG. 13). Accordingly, in such a configuration, current can be simultaneously delivered using the subset of the electrodes without using the remaining electrodes, as the remaining electrodes overlap the subset of electrodes. In such an embodiment, determining which electrodes to use may be accomplished by determining which electrodes have the best tissue contact. By using less than all electrodes, the total energy delivered by the hoop catheter is reduced.

Irreversible electroporation through a multielectrode hoop catheter may enable pulmonary vein isolation in as few as one shock per vein, which may produce much shorter procedure times compared to sequentially positioning a radiofrequency (RF) ablation tip around a vein.

It should be understood that while the energization strategies are described as involving DC pulses, embodiments may use variations and remain within the spirit and scope of the invention. For example, exponentially-decaying pulses, exponentially-increasing pulses, and combinations may be used.

It should be understood that the mechanism of cell destruction in electroporation is not primarily due to heating effects, but rather to cell membrane disruption through application of a high-voltage electric field. Thus, electroporation may avoid some possible thermal effects that may occur when using radio frequency (RF) energy. This "cold therapy" thus has desirable characteristics.

With this background, and now referring again to FIG. 1, system 10 includes a catheter electrode assembly 12 including at least one catheter electrode configured to be used as briefly outlined above and as described in greater detail below. Electrode assembly 12 is incorporated as part of a medical device such as a catheter 14 for electroporation therapy of tissue 16 in a body 17 of a patient. In the illustrative embodiment, tissue 16 comprises heart or cardiac tissue. It should be understood, however, that embodiments may be used to conduct electroporation therapy with respect to a variety of other body tissues.

FIG. 1 further shows a plurality of return electrodes designated 18, 20, and 21, which are diagrammatic of the body connections that may be used by the various sub-systems included in the overall system 10, such as an electroporation generator 26, an electrophysiology (EP) monitor such as an ECG monitor 28, a localization and navigation system 30 for visualization, mapping and navigation of internal body structures. In the illustrated embodiment, return electrodes 18, 20, and 21 are patch electrodes. It should be understood that the illustration of a single patch electrode is diagrammatic only (for clarity) and that such sub-systems to which these patch electrodes are connected may, and typically will, include more than one patch (body surface) electrode. In other embodiments, return electrodes 18, 20, and 21 may be any other type of electrode suitable for use as a return electrode including, for example, one or more catheter electrodes. Return electrodes that are catheter electrodes may be part of electrode assembly 12 or part of a separate catheter (not shown). System 10 may further include a main computer system 32 (including an electronic control unit 50 and data storage-memory 52), which may be integrated with system 30 in certain embodiments. System 32 may further include conventional interface components, such as various user input/output mechanisms 34 *a* and a display 34 *b*, among other components.

Electroporation generator 26 is configured to energize the electrode element(s) in accordance with an electroporation energization strategy, which may be predetermined or may be user-selectable. For electroporation-induced primary necrosis therapy, generator 26 may be configured to produce an electric current that is delivered via electrode assembly 12 as a pulsed electric field in the form of short-duration DC pulses (e.g., a nanosecond to several milliseconds duration, 0.1 to 20 ms duration, or any duration suitable for electroporation) between closely spaced electrodes capable of delivering an electric field strength (i.e., at the tissue site) of about 0.1 to 1.0 kV/cm. The amplitude and pulse duration needed for irreversible electroporation are inversely related. As pulse durations are decreased, the amplitude must be increased to achieve electroporation.

Electroporation generator 26, sometimes also referred to herein as a DC energy source, is a monophasic electroporation generator 26 configured to generate a series of DC energy pulses that all produce current in the same direction. In other embodiments, electroporation generator is biphasic or polyphasic electroporation generator configured to produce DC energy pulses that do not all produce current in the same direction. In some embodiments, electroporation generator 26 is a monophasic defibrillator. The defibrillator is configured to output energy in DC pulses at selectable energy levels, such as fifty joules, one hundred joules, two hundred joules, and the like. Other embodiments may have more or fewer energy settings and the values of the available setting may be the same or different. For successful electroporation, some embodiments utilize the two hundred joule output level. Electroporation generator 26 may output a DC pulse having a peak magnitude of about between about negative one kilovolt (kV) and about negative two kV at the two hundred joule output level. In some embodiments, electroporation generator 26 outputs a DC pulse having a peak magnitude of about between about negative 1.5 kV and about negative 2.0 kV. Other embodiments may output any other suitable voltage, including a positive voltage. In some embodiments, the monophasic defibrillator is a Lifepak 9 defibrillator available from Physio-Control, Inc., of Redmond, Wash., USA.

A variable impedance 27 allows the impedance of the system to be varied to limit arcing from the catheter electrode of catheter 14. Moreover, variable impedance 27 may be used to change one or more characteristics, such as amplitude, duration, pulse shape, and the like, of an output of electroporation generator 26. Although illustrated as a separate component, variable impedance 27 may be incorporated in catheter 14 or generator 26. Variable impedance 27 includes one or more impedance elements, such as resistors, capacitors, or inductors (not shown) connected in series, parallel, or combinations of series and/or parallel. In the illustrated embodiment, variable impedance 27 is connected in series with catheter 14. Alternatively, the impedance elements of variable impedance 27 may be connected in parallel with catheter 14 or in a combination of series and parallel with catheter 14. Moreover, in other embodiments, the impedance elements of variable impedance 27 are connected in series and/or parallel with return electrode 18. Some embodiments include more than one variable impedance 27, each of which may include one or more impedance elements. In such embodiments, each variable impedance 27 may be connected to a different catheter electrode or group of catheter electrodes to allow the impedance through each catheter electrode or group of catheter electrodes to be separately varied.

In the illustrative embodiment, the variable impedance is a variable resistance. In some embodiments variable impedance 27 includes one or more resistors (not shown) removably connected between generator 26 and catheter 14. The resistors may be connected in series, parallel, or any combination of series and parallel connections to produce a desired system impedance. Some or all of the resistors may be added, removed, or connected differently to vary the system impedance. In some other embodiments, variable impedance 27 is variable resistor, such as a rheostat or a potentiometer. In still other embodiments, variable impedance 27 includes resistors coupled together by one or more switches to allow the resistors to be selectively switched in and out of the connection between generator 26 and catheter 14. Such a variable impedance 27 may also be configured to allow some or all of the resistors to be selectively connected together in series or in parallel with each other. In some embodiments, variable impedance 27 is variable in response to an appropriate control signal from computer system 32. The resistors may be any suitable type of resistor. In all embodiments, the resistors (or other impedance elements) have relatively high energy ratings sufficient to handle the output of generator 26 without being damaged. In some embodiments, variable impedance 27 includes Ohmite PulsEater resistors available from Ohmite Mfg. Co. of Warrenville, Ill., USA. With continued reference to FIG. 1, as noted above, catheter 14 may comprise functionality for electroporation and in certain embodiments also an ablation function (e.g., RF ablation). It should be understood, however, that in those embodiments, variations are possible as to the type of ablation energy provided (e.g., cryoablation, ultrasound, etc.).

In the illustrative embodiment, catheter 14 includes a cable connector or interface 40, a handle 42, and a shaft 44 having a proximal end 46 and a distal 48 end. Catheter 14 may also include other conventional components not illustrated herein such as a temperature sensor, additional electrodes, and corresponding conductors or leads. The connector 40 provides mechanical and electrical connection(s) for cable 56 extending from generator 26. The connector 40 may comprise conventional components known in the art and as shown is disposed at the proximal end of catheter 14.

Handle 42 provides a location for the clinician to hold catheter 14 and may further provide means for steering or the guiding shaft 44 within body 17. For example, handle 42 may include means to change the length of a guidewire extending through catheter 14 to distal end 48 of shaft 44 or means to steer shaft 44. Moreover, in some embodiments, handle 42 may be configured to vary the shape, size, and/or orientation of a portion of the catheter. Handle 42 is also conventional in the art and it will be understood that the construction of handle 42 may vary. In an alternate exemplary embodiment, catheter 14 may be robotically driven or controlled. Accordingly, rather than a clinician manipulating a handle to advance/retract and/or steer or guide catheter 14 (and shaft 44 thereof in particular), a robot is used to manipulate catheter 14. Shaft 44 is an elongated, tubular, flexible member configured for movement within body 17. Shaft 44 is configured to support electrode assembly 12 as well as contain associated conductors, and possibly additional electronics used for signal processing or conditioning. Shaft 44 may also permit transport, delivery and/or removal of fluids (including irrigation fluids and bodily fluids), medicines, and/or surgical tools or instruments. Shaft 44 may be made from conventional materials such as polyurethane and defines one or more lumens configured to house and/or transport electrical conductors, fluids or surgical tools. Shaft 44 may be introduced into a blood vessel or other structure within body 17 through a conventional introducer. Shaft 44 may then be advanced/retracted and/or steered or guided through body 17 to a desired location such as the site of tissue 16, including through the use of guidewires or other means known in the art.

In some embodiments, catheter 14 is a hoop catheter having catheter electrodes (not shown) distributed about one or more hoops at the distal end of shaft 44. The diameter of the hoop(s) may be variable. In some embodiments, the hoop catheter has a maximum diameter of about twenty-seven millimeters (mm). In some embodiments, the hoop diameter is variable between about fifteen mm and about twenty eight mm. Alternatively, the catheter may be a fixed diameter hoop catheter or may be variable between different diameters. In some embodiments, catheter 14 has fourteen catheter electrodes. In other embodiments, catheter 14 includes ten catheter electrodes, twenty catheter electrodes, or any other suitable number of electrodes for performing electroporation. In some embodiments, the catheter electrodes are ring electrodes, such as platinum ring electrodes. Alternatively, the catheter electrodes may be any other suitable type of electrodes, such as single sided electrode or electrodes printed on a flex material. In various embodiments, the catheter electrodes have lengths of 1.0 mm, 2.0 mm, 2.5 mm, and/or any other suitable length for electroporation.

FIGS. 12 and 13 show the distal end of an example variable diameter hoop catheter 1200 usable as catheter 14. Hoop catheter 1200 includes fourteen catheter electrodes 1202. Catheter electrodes 1202 are ring electrodes. In FIG. 12, hoop catheter 1200 is shown in its fully expanded configuration with a diameter 1204 of about twenty-eight millimeters (mm). In FIG. 13, hoop catheter 1200 is shown in its fully contracted configuration with a diameter of about fifteen mm. In other embodiments, catheter 1200 may be variable between different diameters and/or may include any other suitable number of electrodes for performing electroporation. Additional catheters that may be suitable for use as catheter 14 are discussed below with respect to FIGS. 14-20.

The localization and navigation system 30 may be provided for visualization, mapping and navigation of internal body structures. System 30 may comprise conventional apparatus known generally in the art (e.g., an EnSite NAVX™ Navigation and Visualization System, commercially available from Abbott Laboratories. and as generally shown with reference to commonly assigned U.S. Pat. No. 7,263,397 titled "Method and Apparatus for Catheter Navigation and Location and Mapping in the Heart," the entire disclosure of which is incorporated herein by reference). It should be understood, however, that this system is exemplary only and not limiting in nature. Other technologies for locating/navigating a catheter in space (and for visualization) are known, including for example, the CARTO navigation and location system of Biosense Webster, Inc., the AURORA® system of Northern Digital Inc., commonly available fluoroscopy systems, or a magnetic location system such as the gMPS system from Mediguide Ltd. In this regard, some of the localization, navigation and/or visualization system would involve a sensor be provided for producing signals indicative of catheter location information, and may include, for example one or more electrodes in the case of an impedance-based localization system, or alternatively, one or more coils (i.e., wire windings) configured to detect one or more characteristics of a magnetic field, for example in the case of a magnetic-field based localization system.

Several factors may influence the formation of electrical arcs from catheter electrodes in an electroporation system, such as system 10. In general, the various factors combine to define in a maximum energy that can be delivered by an electroporation generator to a catheter in a single pulse without causing arcing from the catheter. The total electrode surface area is a strong determinant of the maximum allowable energy which can be safely delivered in a single pulse without arcing from the catheter electrode(s). The total electrode surface area is the sum of all individual electrode surface areas. The catheter shape is another determinant of the maximum allowable pulse energy. For example when a catheter hoop is deployed in the minimum possible diameter, the threshold for arcing is lower than when the hoop is deployed in the maximum diameter. The time between individual energy applications is another determinant of the maximum allowable pulse energy. For example when one pulse is "followed quickly" by a second pulse, the arc threshold on the second pulse is lower than the threshold for the first pulse, because some of the gas bubbles which were created on the electrode by the first pulse are still present when the second pulse is applied. The formation of the insulating gas layer on the electrode is cumulative, and if/when the layer forms a complete insulator an arc can occur. This effect has been observed in pulses applied about 30 seconds apart (i.e. it is not only a short-duration phenomenon).

Figure 2:
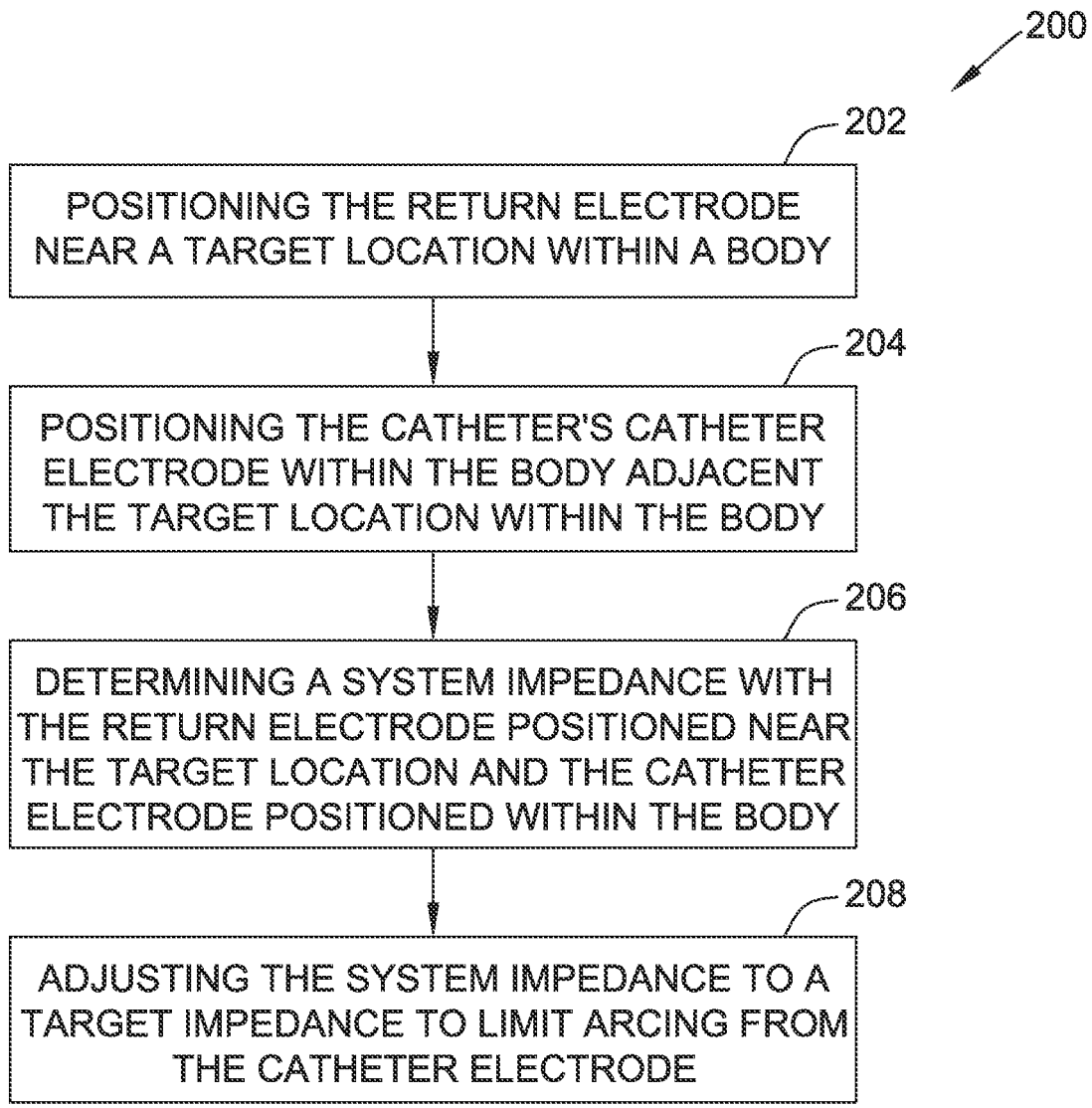
FIG. 2 is flowchart of a method of controlling an electroporation system, such as the system shown in FIG. 1.

FIG. 2 is a flowchart of a method 200 of controlling an electroporation system, such as system 10 shown in FIG. 1. Although method 200 will be described with reference to system 10, it should be understood that method 200 may be performed using any suitable electroporation system including a DC energy source, a return electrode connected to the DC energy source, and a catheter including a catheter electrode connected to the DC energy source. The method includes positioning, at 202, return electrode 18 near a target location within body 17. As used herein, a return electrode is near a target location when positioned on or in a body sufficiently close to the target location to allow electroporation to be performed. For example, a return electrode 18 that is part of a catheter (whether the catheter 14 or a separate catheter) may be positioned in the body adjacent the target location. In embodiments in which return electrode 18 is a patch electrode, the return electrode is positioned on an external surface of body 17 near the target location. In other embodiments, the return electrode is positioned within body 17 near the target location. At 204, the method includes positioning the catheter's catheter electrode within body 17 adjacent the target location, e.g., adjacent tissue 16.

At 206, the system impedance is determined with return electrode 18 positioned near the target location and the catheter electrode positioned within body 17. The system impedance may be determined using any suitable method for determining the system impedance. In some embodiments, the catheter electrodes are shorted together and a known (non-electroporation) signal is output by generator 26 to catheter 14. The response of system 10 is measured and the system impedance is calculated. In some embodiments, the system impedance is measured at 485 kilohertz (kHz) using an RF ablation generator. The RF ablation generator may be part of generator 26, or may be a separate RF ablation generator. An example suitable RF ablation generator is an IBI-1500T11 ablation generator available from Abbott Laboratories. In some embodiments, a small (relative to the electroporation voltage) DC voltage is applied to the catheter and the output voltage and current are measured. The resistive impedance is determined according to Ohm's law by dividing the voltage by the current.

The system impedance is adjusted, at 208, to a target impedance to limit arcing from the catheter electrode. The system impedance is adjusted using variable impedance 27. In the example embodiment, the variable impedance is a resistance and resistance may be added or removed as needed to adjust the system impedance to the target impedance. In some embodiments, the target impedance is a range of impedances, such as a resistance between about seventy and eighty ohms. In some embodiments, adjusting the system impedance includes adjusting the system capacitance, inductance, resistance, or a combination thereof. In the example embodiment, the target impedance is a determined resistance that will limit the likelihood of electrical arcing between the catheter electrodes and return electrode 18 when system is used for electroporation. The target impedance is selected primarily based on the particular settings and characteristics of generator 26, characteristics of catheter 14, and a desired maximum (or threshold) current density on the catheter electrodes. The value of the target impedance is selected to keep the current density on the catheter electrodes below a threshold current density to prevent arcing. In various embodiments, the target resistance is selected to keep the current density on the catheter electrodes below about one hundred fifty milliamps per square millimeter ($mA/mm^2$), below about one hundred thirty $mA/mm^2$, below about one hundred twenty $mA/mm^2$, below about one hundred $mA/mm^2$, between about one hundred $mA/mm^2$ and one hundred twenty $mA/mm^2$, or below any threshold current density or in any current density range that is suitable to limit the likelihood of arcing. Multiplying the threshold current density by the surface area of the catheter electrodes produces a desired peak current. If the peak voltage output of the generator at a particular energy setting and in the particular environment (e.g., in body 17) is known, the target impedance to produce that desired peak current can be calculated using Ohm's law. Accordingly, the target system impedance may be determined by:

$$R_{target} = \frac{V_{peak}}{\text{Current Density Threshold} \times \text{Catheter Electrode } SA} \quad (1)$$

Where $R_{target}$ is the target system impedance, $V_{peak}$ is the peak output voltage of generator 26 under current conditions and settings, Current Density Threshold is the target current density to limit arcing, and Catheter Electrode SA is the surface area of the catheter electrodes.

Figure 3:
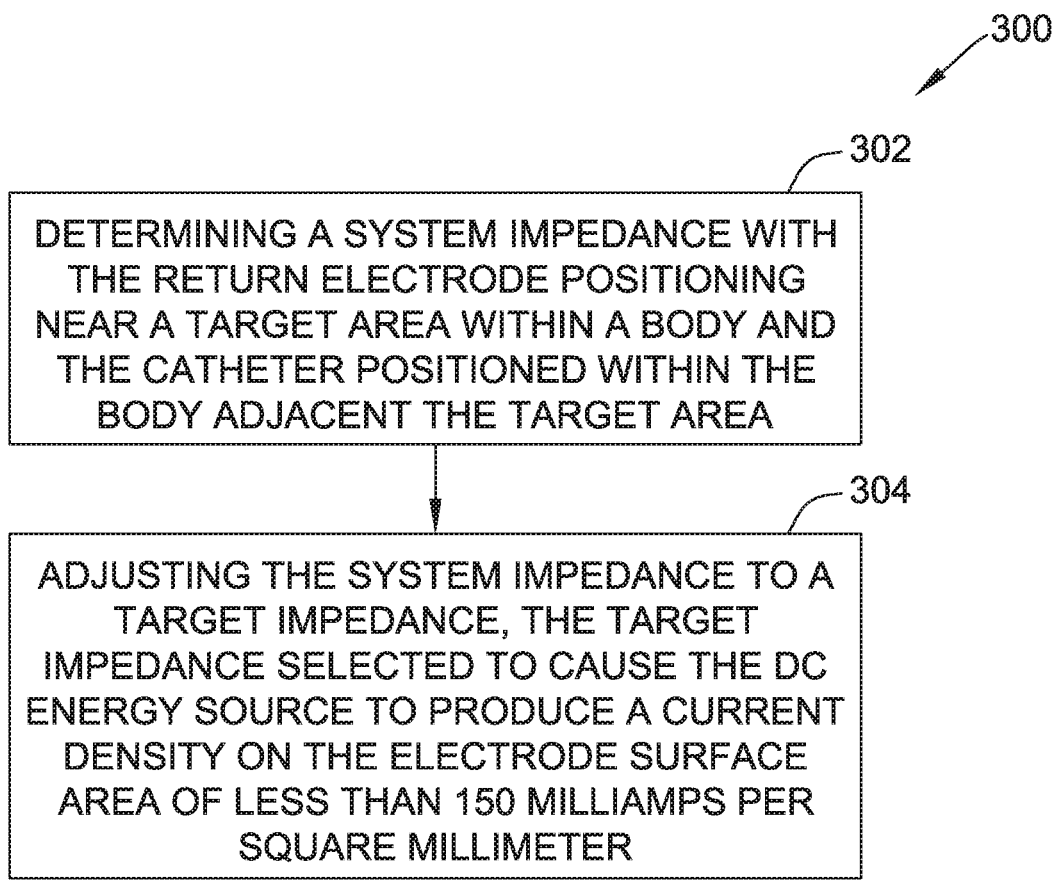
FIG. 3 is flowchart of another method of controlling an electroporation system, such as the system shown in FIG. 1.

FIG. 3 is flowchart of a method 300 of controlling an electroporation system, such as system 10 shown in FIG. 1. Although method 300 will be described with reference to system 10, it should be understood that method 300 may be performed using any suitable electroporation system including a DC energy source, and a catheter connected to the DC energy source and having an electrode surface area. At 302, the system impedance is determined with the patch electrode on a body and the catheter positioned within the body adjacent a target area. At 304, the system impedance is adjusted, e.g., with the variable impedance, to a target impedance. The target impedance is selected to cause the DC energy source to produce a current density on the electrode surface area of less than one hundred fifty $mA/mm^2$. In other embodiments, the target impedance is selected to cause the DC energy source to produce a current density on the electrode surface area of less than one hundred twenty $mA/mm^2$.

Example 1

Figure 4:
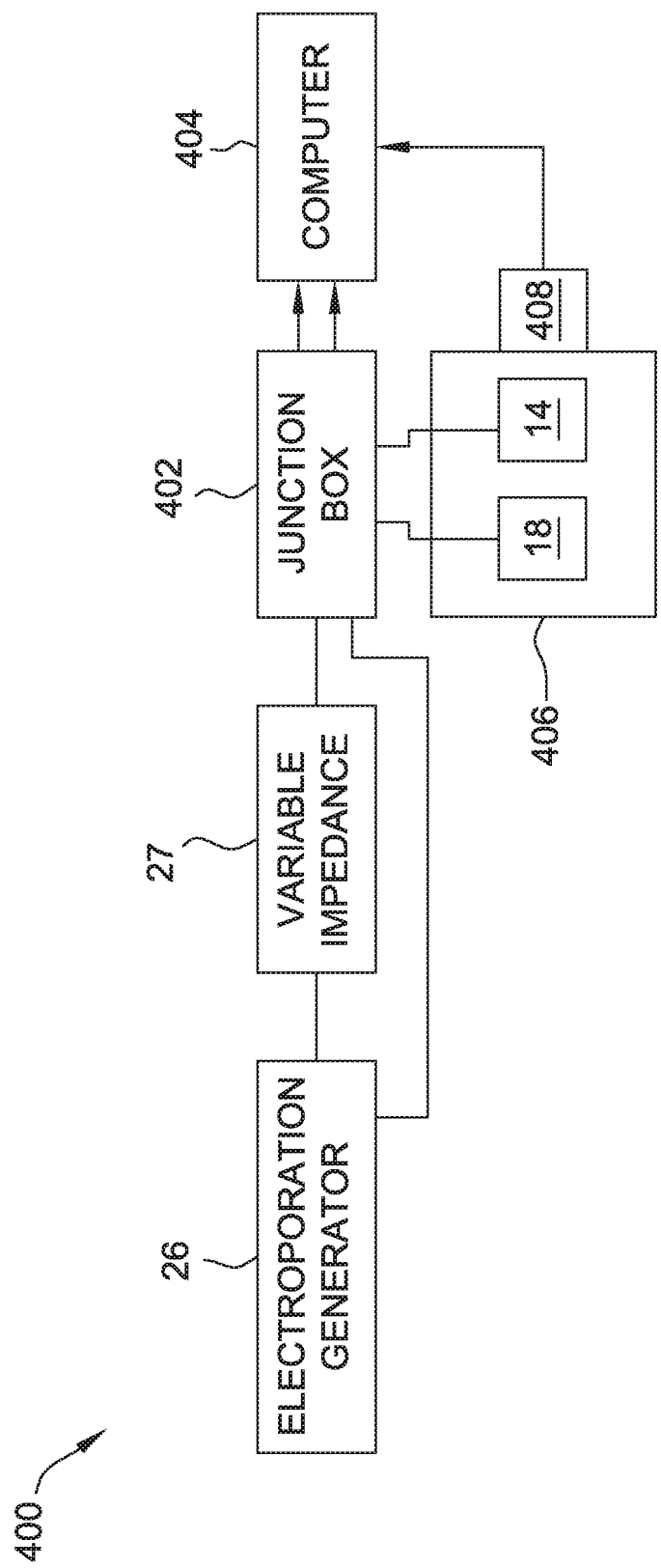
FIG. 4 is a simplified diagram of an example implementation of the system shown in FIG. 1.

An example implementation of system 10 was constructed and tested. FIG. 4 is a simplified diagram of the example system 400. In the example system 400, generator 26 is the Lifepak 9 defibrillator described above. A junction box 402 is used to connect generator 26 (and variable impedance 27) to catheter 14 and return electrode 18. Catheter 14 is a fifteen mm diameter hoop catheter with ten electrodes of two mm length. The surface area of the electrodes is about one hundred forty six square millimeters. Return electrode 18 is a four cm square stainless steel mesh with a much larger surface area than that of the catheter electrodes. The voltage and current supplied to catheter 14 are detected at junction box 402 and monitored by a computing device 404.

Some tests of this implementation were performed with catheter 14 and the return 18 in a tank 406 having a diameter of eleven centimeters (cm). Other tests were performed with the catheter 14 and return 18 in an in vivo pig model (not shown) rather than in tank 406. A pressure transducer 408 is attached to wall of tank 406 with the sensor approximately six cm from the catheter hoop. Tank 406 was filled with 6.7 millisiemens per cm (mS/cm) saline for one set of tests and heparinized bovine blood with conductivity approximately 6.2 mS/cm for a second set of tests. Shocks of fifty, one hundred, and two hundred joules were applied from generator 26 to catheter 14.

Figure 5:
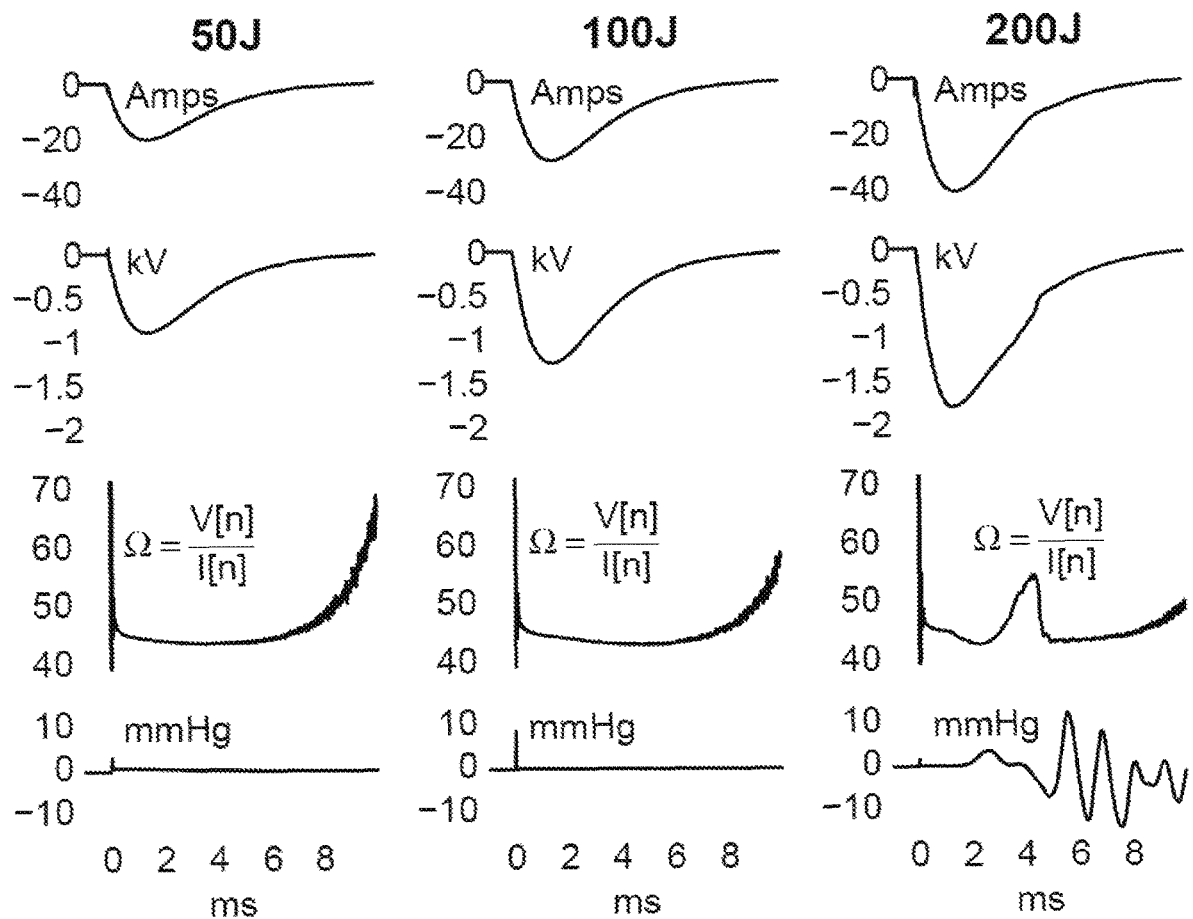
FIG. 5 graphically presents the current, voltage, calculated resistance, and pressure wave from the tests of the example implementation shown in FIG. 4 in saline with the variable resistance at zero ohms.
Figure 6:
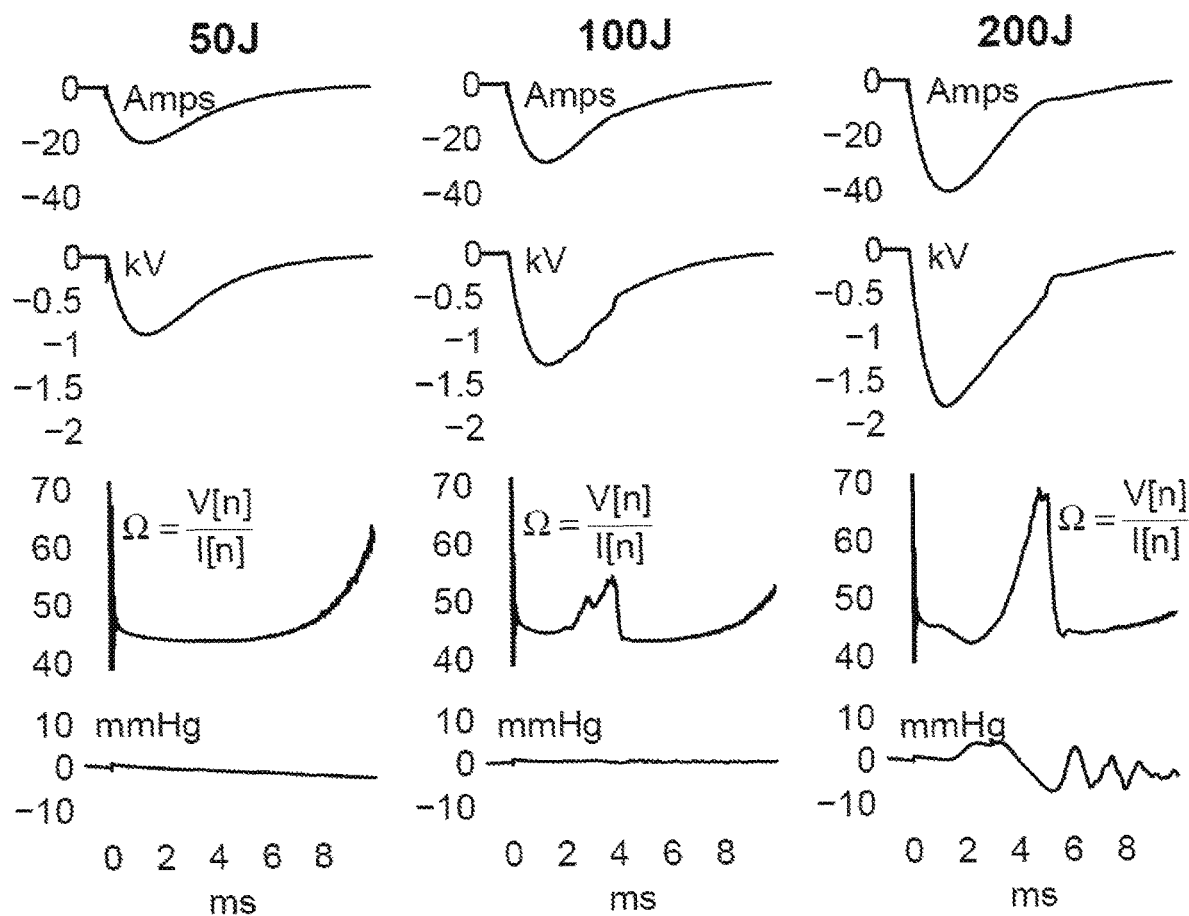
FIG. 6 graphically presents the current, voltage, calculated resistance, and pressure wave from the tests of the example implementation shown in FIG. 4 in bovine blood with the variable resistance at zero ohms.

FIGS. 5 and 6 are graphs of the current, voltage, calculated resistance, and pressure wave from the tests in saline and bovine blood with the variable resistance at zero ohms. In saline (FIG. 5), the fifty and one hundred joule shocks produced smooth waveforms, but the two hundred joule shocks produced a slight deflection in the recovery slope of the current trace and a more obvious deflection at a similar point in the voltage trace. These deflections manifest as the large deflection in the calculated resistance trace. The pressure wave shows large oscillations that correspond to the resulting explosion from an electric arcing event. In blood (FIG. 6), the fifty joule shocks produced smooth waveforms and showed no signs of arcing. The one hundred and two hundred joule shocks, however, have apparent deflections in the current, voltage, and calculated resistance traces, indicating arcing occurred.

Figure 7:
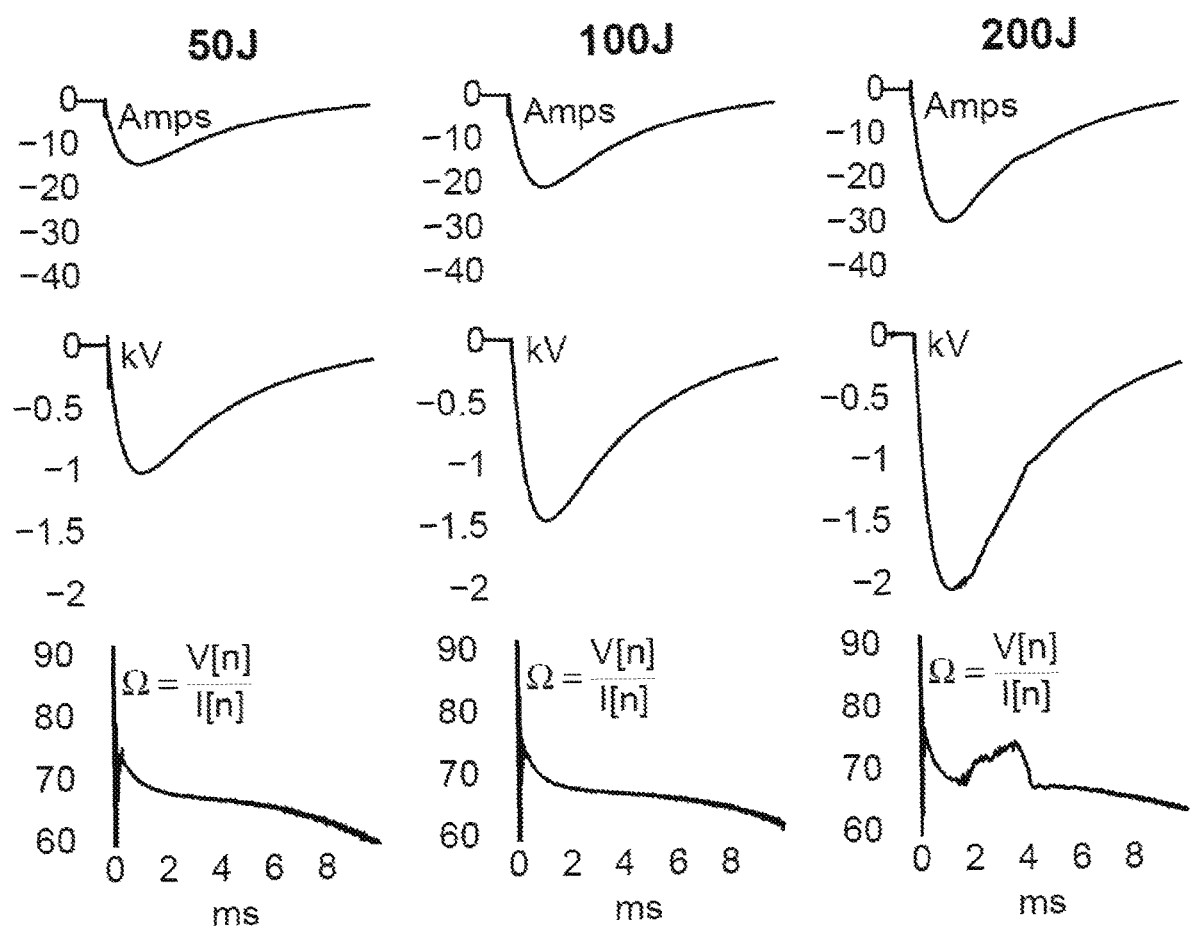
FIG. 7 graphically presents the results from a test in an in vivo pig model with the variable resistance at zero ohms.

FIG. 7 presents the results from a repeat of the test in an in vivo pig model (rather than in tank 406) with variable impedance 27 at zero ohms. The results also show no arcing with fifty and one hundred joule shocks, and arcing during two hundred joule shocks.

Figure 8:
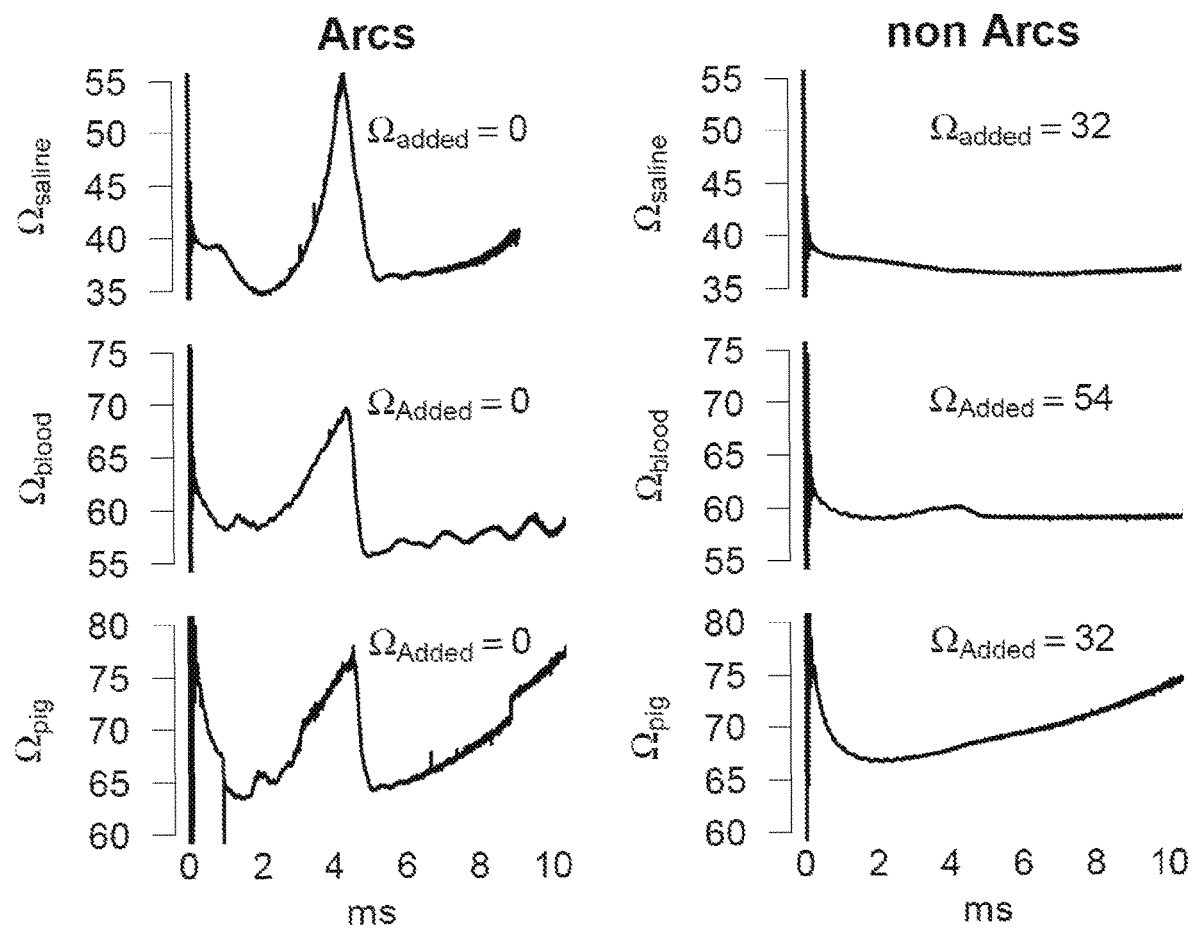
FIG. 8 graphically presents the calculated resistance for two hundred joule shocks in a saline tank, a blood tank, and in an in vivo pig model with the variable resistance at zero ohms and increased to limit arcs.

The saline, bovine blood, and in vivo pig tests were repeated with the system impedance increased using variable impedance 27. Shocks were delivered at two hundred joule and the impedance increased in ten ohm increments until no arc was detected. The delivered current and voltage are measured between the catheter and return. FIG. 8 presents calculated resistance for representative two hundred joule shocks in the saline tank, the blood tank, and in vivo (top to bottom). The left column clearly demonstrates that shocks with variable impedance 27 at zero arced in each model. The right column is the corresponding threshold for a shock with no arcing for each trial. The resistance added by variable impedance 27 in each trial is labelled. The absence of arcing is evidenced by the smooth calculated medium resistance trace.

Figure 9:
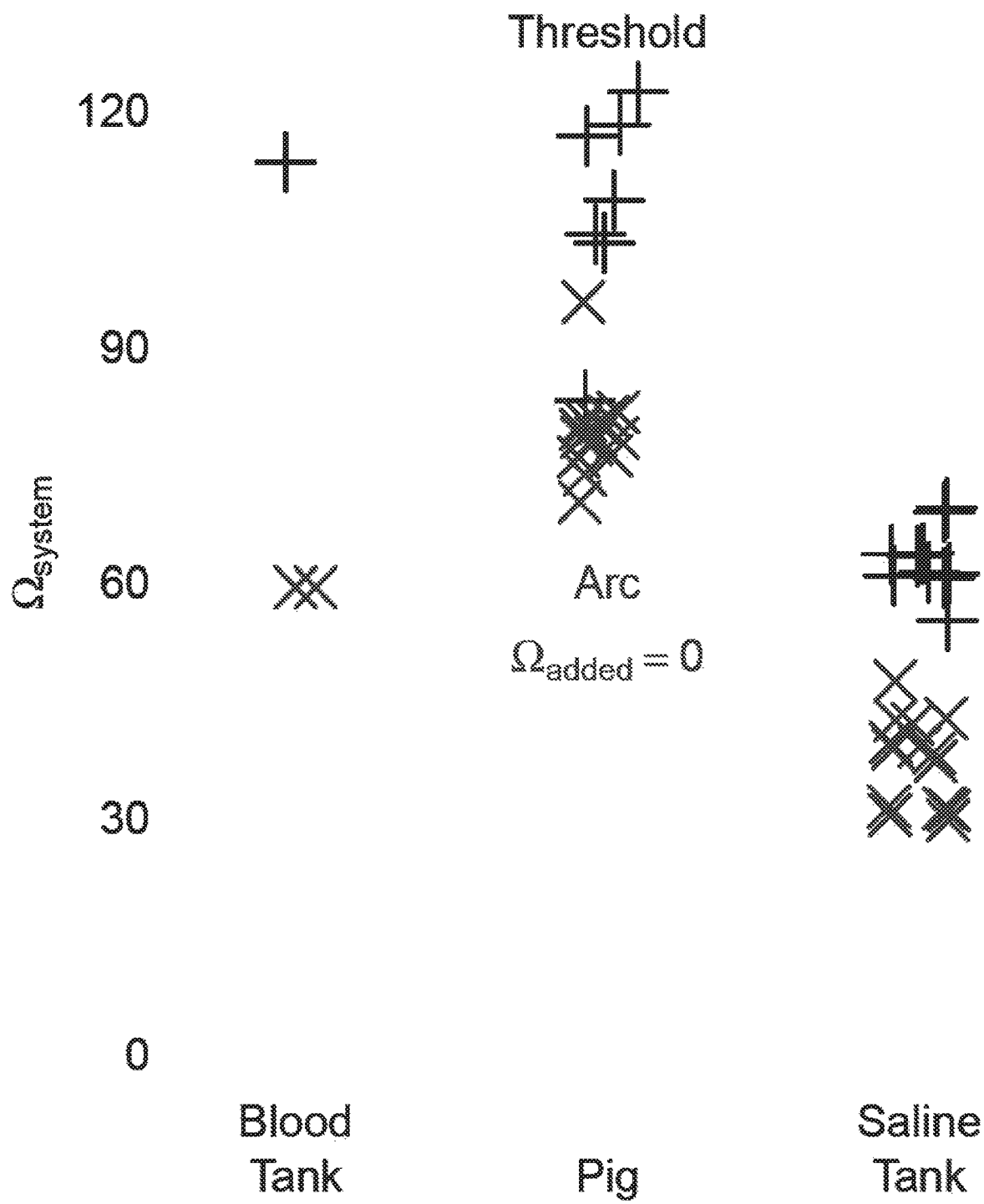
FIG. 9 is a graph of the system impedance at the arc threshold for a saline tank, a blood tank, and in vivo pig.

FIG. 9 summarizes the arc threshold findings as system resistance (y axis=medium resistance+added resistance) for each of the three models (binned on the x axis). Shocks that arced without added resistance are represented by Xs and threshold resistances (system resistance that prevented arcs for each trial) are represented by +s. The blood data set was in better agreement with the in vivo data than was the saline data, which underestimated the system resistance required to prevent shocks. Reframed to mean+/−standard deviation of joules delivered to the test medium, the saline threshold was ninety nine joules+/−nineteen joules (n=10), the blood threshold was one hundred and six joules (n=1), and in vivo threshold was one hundred fifty five joules+/−thirty five joules (n=8).

To limit arcing in the implementation of Example 1, the target impedance to which the system impedance should be adjusted may be set at about one hundred fifty ohms.

Example 2

A second example implementation of system 10 was constructed and tested. The second implementation is the same as the example system 400, but uses a different catheter 14. In the second implementation, catheter 14 is a fourteen electrode hoop catheter with 2.5 mm ring electrodes and a 15-28 mm adjustable hoop size. The electrodes have a surface area of about two hundred fifty six square millimeters.

Figure 10:
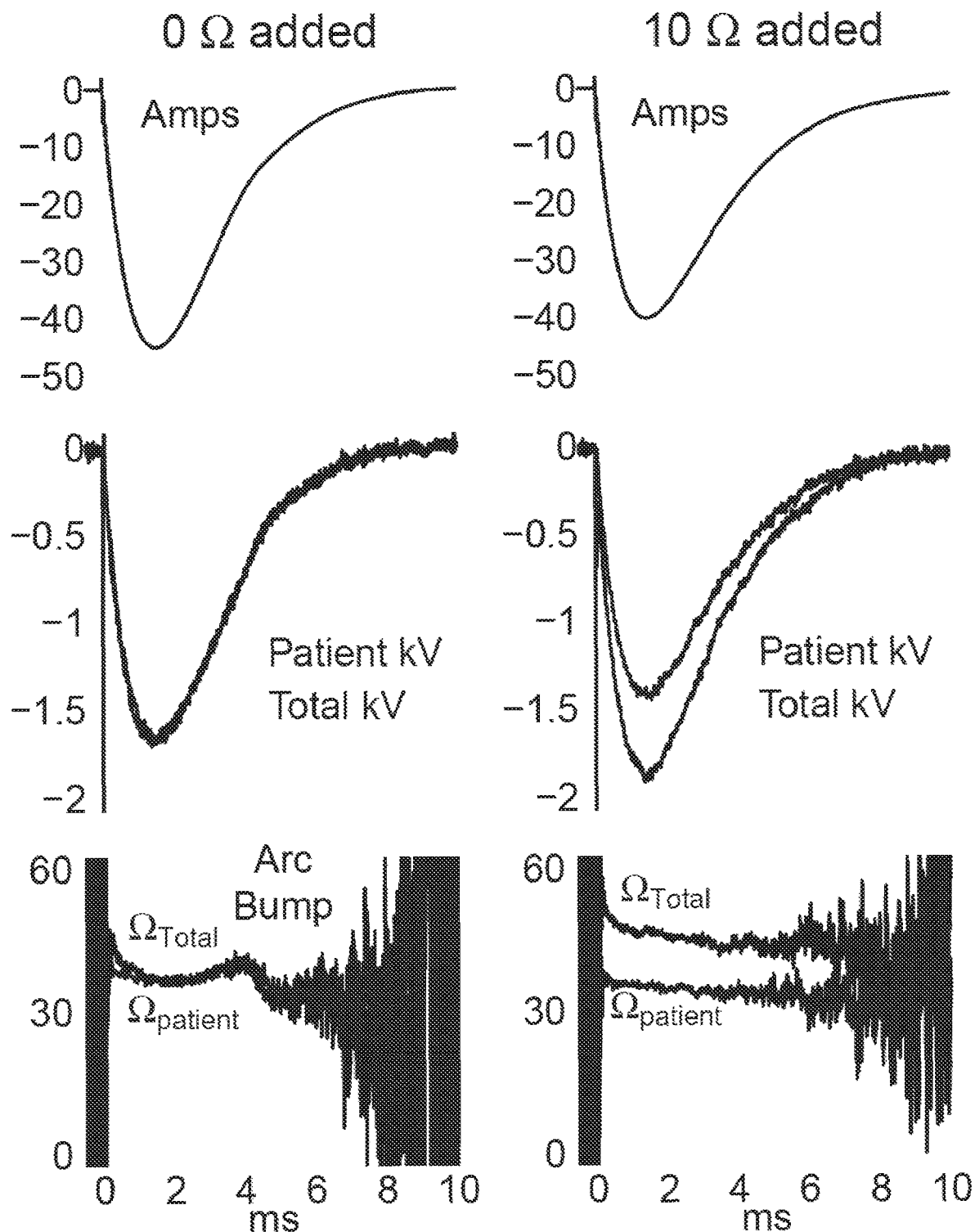
FIG. 10 shows saline tank data indicating arcing for a two hundred joule shock with zero added variable resistance, and indicating no arcing for a two hundred joule shock with a ten ohm added variable resistance.

FIG. 10 shows saline tank data with evidence of arcing (the bump in the impedance trace) when a two hundred joules shock is applied by generator 26 with variable impedance 27 at zero. When the system impedance is increased by ten ohms using variable impedance 27, the traces (right side) do not show any sign of arcing when a two hundred joule shock is applied. The tests were repeated multiple times to collect multiple current, voltage, and calculated resistance traces from two hundred joule shocks in the saline tank. Based on test data, a target impedance for the system impedance for the system in Example 2 is about seventy ohms. In vivo testing was performed using the Example 2 implementation of system 10 set at two hundred joules. Variable impedance 27 was used to adjust the system impedance to about 70 for the trials and no arcing was observed.

Figure 11:
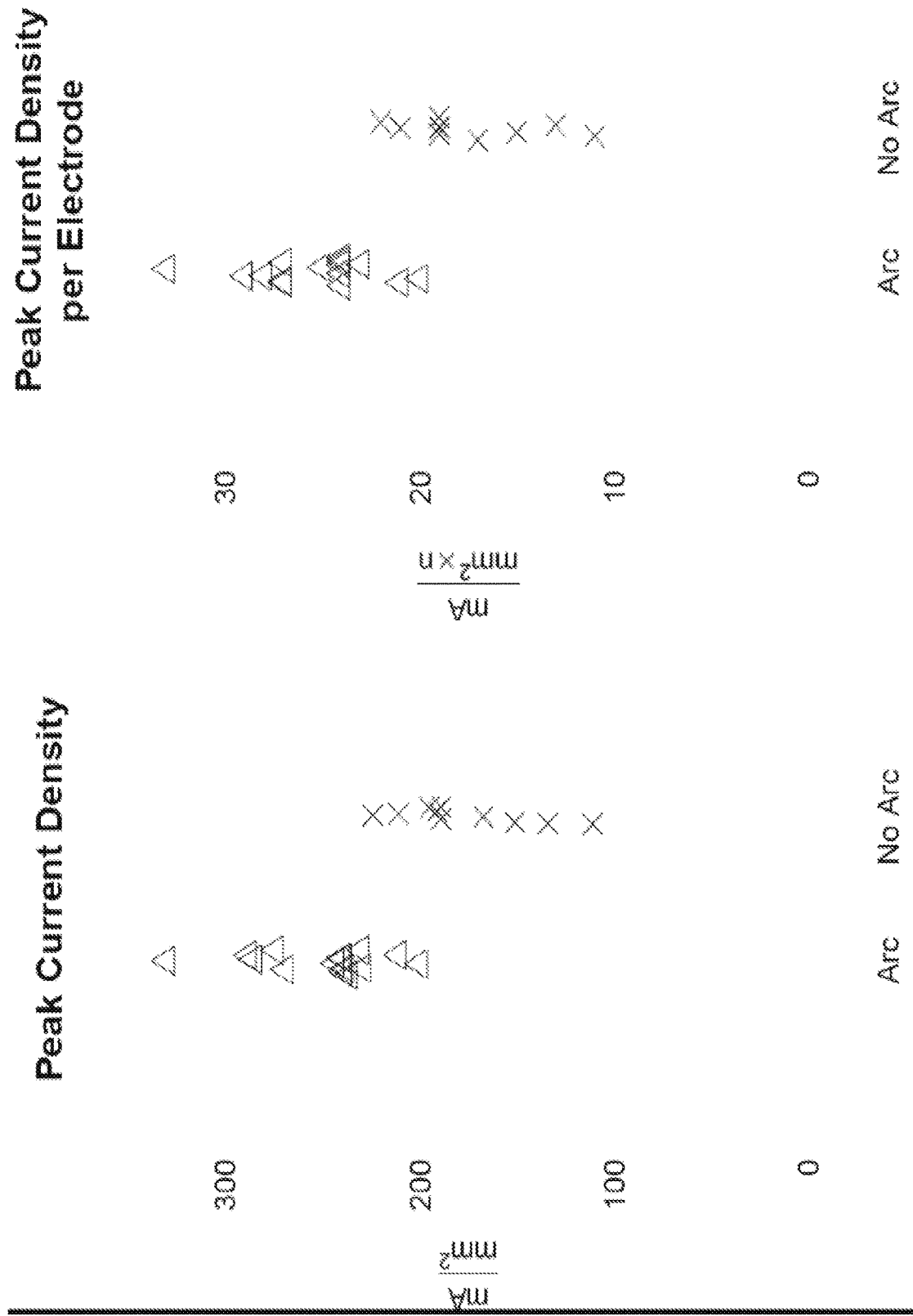
FIG. 11 is a graph of results from a test performed to determine the current density at which arcing occurs when using a monophasic defibrillator as an electroporation generator.

FIG. 11 is a graph of results from a test performed to determine the current density at which arcing occurs when using a monophasic defibrillator as generator 26, such as in the systems of Examples 1 and 2. A length of a stainless steel rod was positioned in a saline tank and connected to the defibrillator as the shock anode. A hoop catheter with ten 2.0 mm length electrodes was connected to the defibrillator as the cathode and positioned in the saline tank. Multiple trials of two hundred joule shocks by the defibrillator were conducted. The amount of the stainless steel rod submerged in the tank was varied during the trials to vary the electrode surface area. The collected data is plotted in FIG. 11 and shows a transition from arcing shocks to non-arcing shocks occurred when the total current density dropped below about two hundred mA/mm$^2$.

Various additional experiments were performed to determine threshold current densities below which arcing was unlikely to occur. A first set of experiments were performed using a ten electrode catheter with 2.0 mm ring electrodes and a twenty electrode catheter with 1.0 mm ring electrodes in blood, in vivo pig, and in saline. Table 1, below, presents the mean of the largest current density (in mA/mm$^2$) achieved without arcing.

TABLE 1

| | Current Density (No Arc) | | | | | |
|---|---|---|---|---|---|---|
| | Ten Electrodes (2.0 mm length) | | | Twenty Electrodes (1.0 mm length) | | |
| | Mean | Std Dev | n | Mean | Std Dev | n |
| blood | 141 | NA | 1 | 129 | NA | 1 |
| in vivo pig | 151 | 20 | 7 | 195 | 20 | 6 |
| saline | 209 | 13 | 10 | 208 | 40 | 8 |

Table 2, below, was compiled from data similarly comparing a fourteen electrode catheter with 2.5 mm ring electrodes to a ten electrode catheter with 2.0 mm long ring electrodes. It shows the mean of largest current density (in mA/mm$^2$) observed without arc. The saline data was collected with the catheter hoop in saline and contact with bovine heart tissue.

TABLE 2

| | Current Density (No Arc) | | | | | |
|---|---|---|---|---|---|---|
| | Ten Electrodes (2.0 mm length) | | | Fourteen Electrodes (2.5 mm length) | | |
| | Mean | Std Dev | n | Mean | Std Dev | n |
| blood | 133 | 6 | 15 | 138 | 19 | 17 |
| Saline + tissue | 179 | 24 | 2 | 156 | 6 | 2 |

Peak current (in amperes) for the data set in the Table 2 is shown in Table 3 below. The electrode surface area of the fourteen electrode catheter is about two hundred fifty six square millimeters. The ten electrode catheter had a surface area of about one hundred forty six square millimeters.

TABLE 3

| | Peak Current | | | | | |
|---|---|---|---|---|---|---|
| | Ten Electrodes (2.0 mm length) | | | Fourteen Electrodes (2.5 mm length) | | |
| | Mean | Std Dev | n | Mean | Std Dev | n |
| blood | 19 | 1 | 15 | 35 | 5 | 17 |
| Saline + tissue | 26 | 4 | 2 | 40 | 0 | 2 |

Based on the data presented above, a current density threshold may be established for use with systems and methods described herein. The data suggests electroporation pulse arcs require a current density in excess of one hundred fifty to two hundred mA/mm$^2$ in animals. Thus, in some embodiments, a current density threshold is set at one hundred fifty mA/mm$^2$. In some embodiments, the current density threshold is set between about one hundred and about one hundred twenty mA/mm$^2$ to maintain therapy while preventing arcs. In some embodiments, the current density threshold is set at about one hundred twenty mA/mm$^2$ to provide about a twenty percent margin of safety from the one hundred fifty mA/mm$^2$ current density above which arcing seems to occur. In other embodiments, the current density threshold is set at any other suitable value high enough to allow irreversible electroporation to occur and low enough to prevent arcing.

As discussed above, the target system impedance can then be determined for any particular implementation of system 10 based on the selected current density threshold, the surface area of the catheter electrodes, and the peak output voltage of generator 26.

In some embodiments, a variable diameter, high output hoop catheter may be used for electroporation procedures. Such a catheter may be used with the systems and methods described above, such as, for example, with system 10 and/or with other electroporation generators and systems. Several example embodiments of variable diameter, high output hoop catheters are described below with reference to FIGS. 14-20.

FIGS. 14-17 illustrate an example variable diameter, high output hoop catheter 1400 usable, in some embodiments, as catheter 14. As described in greater detail below, hoop catheter 1400 is configured to safely handle an electrical input in the range of ten amperes and/or one thousand volts.

Figure 14:
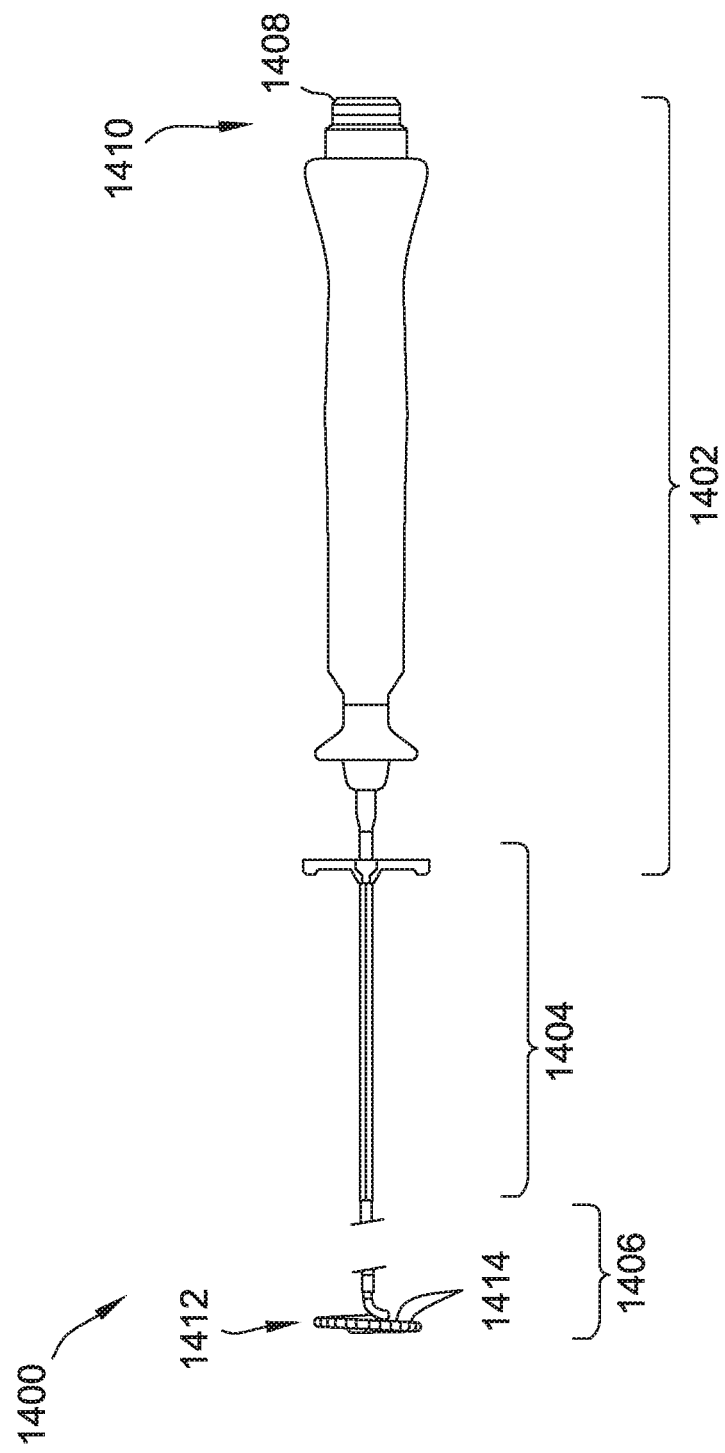
FIG. 14 is a variable diameter, high output hoop catheter in an expanded configuration.

Referring first to FIG. 14, hoop catheter 1400 includes a handle 1402, a shaft 1404, a distal loop subassembly 1406, and a connector 1408. Hoop catheter 1400 has a proximal end 1410 and a distal end 1412. As used herein, "proximal" refers to a direction toward the portion of the catheter 12 near the clinician, and "distal" refers to a direction away from the clinician and (generally) inside the body of a patient.

Connector 1408 provides mechanical, fluid, and electrical connection(s) for cables, such as, for example, electrical cables (not shown) and/or other components of system 10 (e.g., a visualization, navigation, and/or mapping system, an ablation generator, irrigation source, etc.). Connector 1408 is disposed at a proximal end 1410 of hoop catheter 1400, and handle 1408 thereof, in particular. In the example embodiment, connector 1408 is a waterproof connector. In other embodiments, connector is water resistant connector. In some embodiments, connector 1408 is not itself waterproof, but includes a waterproof element to protect the connector from liquids and moisture, such as a waterproof or water resistant sheath. Connector 1408 further includes an insulator or insulating material (not shown), such that connector 1408 is suitable for conducting voltages in the range of one thousand volts and electrical current in the range of ten amps. In the example embodiment, connector 1408 is used to couple catheter 1400 to an electroporation generator, such as electroporation generator 26.

Handle 1402, which is disposed at proximal end 1410 of shaft 1404, provides a location for the clinician to hold catheter 1400 and may further provide means for steering or guiding shaft 1404 within the body of the patient. Handle 1402 may include means to change the length of a steering wire extending through catheter 1400 to distal end 30 of shaft 1404 to steer shaft 1404. In other embodiments, catheter 1400 may be robotically driven or controlled. Accordingly, rather than a clinician manipulating a handle to steer or guide catheter 1400 and shaft 1404 thereof, in such an embodiments, a robot is used to manipulate catheter 1400. In various embodiments, handle 1402 is a FLEXABILITY Uni-D handle with modifications configured to increase pull wire travel. Handle 1402 may further include an 8F shaft lug and flush port plug. Handle 1402 is at least partially hollow to define an interior channel (not shown) therethrough.

Shaft 1404 is an elongate, tubular, flexible member configured for movement within body 18. A pull wire (not shown in FIG. 14) for adjusting the diameter of the hoop and electrical conductors (not shown in FIG. 14) connected between electrodes at distal end 1412 and connector 1408 are disposed within an interior channel (not shown) defined by shaft 1404. Shaft 1404 may also permit transport, delivery, and/or removal of fluids (including irrigation fluids, cryogenic ablation fluids, and bodily fluids), medicines, and/or surgical tools or instruments. Shaft 1404 may be made from conventional materials such as polyurethane, and defines one or more lumens configured to house and/or transport electrical conductors, fluids, or surgical tools. Shaft 1404 may be introduced into a blood vessel or other structure within the body 18 through a conventional introducer. Shaft 1404 may then be steered or guided through body 18 to a desired location, such as heart 20, using means well known in the art. Shaft 1404 houses electrode wires (not shown in FIG. 14) for carrying electrical current to electrodes 1414. Electrode wires extend between handle 1402 and electrodes 1414 within an interior portion of shaft 1404. To this end, shaft 1404 may include an insulator or insulating material. For example, shaft 1404 may be packed with an insulation material and/or a cylindrical layer of insulation material may be circumferentially disposed within an interior portion of shaft 1404. The thickness and material characteristics of such insulation are selected to configure shaft 1404 for safe use with voltage and current in the range of one thousand volts and/or ten amperes.

Catheter electrodes 1414 mounted on distal loop subassembly 1406 may be used for a variety of diagnostic and therapeutic purposes including, for example and without limitation, electroporation, electrophysiological studies, pacing, cardiac mapping, and ablation. In a preferred embodiment, catheter electrodes 1414 are configured for use as electroporation electrodes. In some embodiments, catheter electrodes 1414 may be configured for additional uses. For example, one or more of catheter electrodes 1414 may perform a location or position sensing function. More particularly, one or more of catheter electrodes 1414 may be configured to be a positioning sensor(s) that provides information relating to the location (position and orientation) of catheter 1400, and distal end 1412 of shaft 1404 thereof, in particular, at certain points in time. Accordingly, as catheter 1400 is moved along a surface of a structure of interest of heart 20 and/or about the interior of the structure, the sensor(s) can be used to collect location data points that correspond to the surface of, and/or other locations within, the structure of interest. These location data points can then be used by, for example, model construction system 14, in the construction of a three-dimensional model of the structure of interest. In other embodiments, separate catheter electrodes are used for electroporation and positioning.

Figure 15:
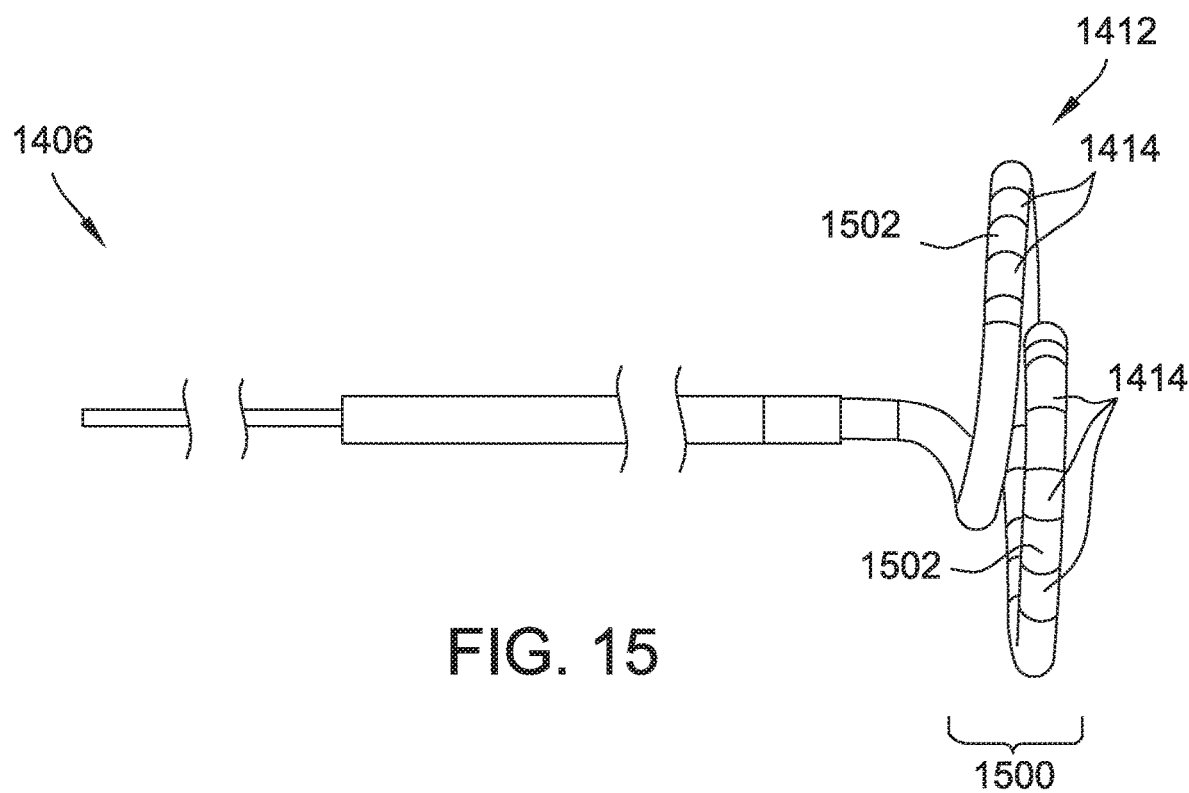
FIG. 15 is a distal loop subassembly of the hoop catheter of FIG. 14
Figure 16:
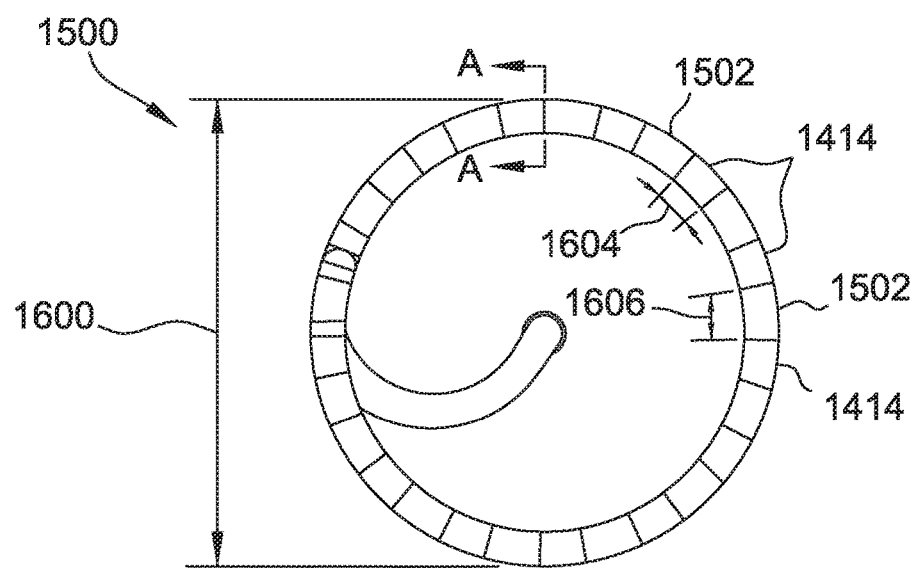
FIG. 16 is a top view of the distal loop subassembly of FIG. 15.

FIGS. 15 and 16 are views of distal loop subassembly 1406. Specifically, FIG. 15 is a side view of distal loop subassembly 1406 with a variable diameter loop 1500 at distal end 1412. FIG. 15 is a top view of variable diameter loop 1500 of distal loop subassembly 1406.

Variable diameter loop 1500 is variable between an expanded (also referred to as "open") diameter 1600 (shown in FIG. 16) and a retracted (also referred to as "closed") diameter 1600 (not shown). In the example embodiment, the expanded diameter 1600 is twenty seven mm and a retracted diameter 1600 of fifteen mm. In other embodiments, diameter 1600 may be variable between any suitable open and closed diameter 1600.

Variable diameter loop 1500 includes fourteen catheter electrodes 1414 evenly spaced around the circumference of variable diameter loop 1500. Catheter electrodes 1414 are platinum ring electrodes configured to conduct and/or discharge electrical current in the range of one thousand volts and/or ten amperes. In other embodiments, variable diameter loop 1500 may include any suitable number of catheter electrodes 1414 made of any suitable material. Catheter electrodes 1414 may comprise any catheter electrode suitable to conduct high voltage and/or high current (e.g., in the range of one thousand volts and/or ten amperes). Each catheter electrode 1414 is separated from each other catheter electrode by an insulated gap 1502. In the example embodiment, each catheter electrode 1414 has a same length 1604 (shown in FIG. 16) and each insulated gap 1502 has a same length 1606 as each other gap 1502. Length 1604 and length 1606 are both about 2.5 mm in the example embodiment. In other embodiments, length 1604 and length 1606 may be different from each other. Moreover, in some embodiments, catheter electrodes 1414 may not all have the same length 1604 and/or insulated gaps 1502 may not all have the same length 1606. In some embodiments, catheter electrodes 1414 are not spaced evenly around the circumference of variable diameter loop 1500.

Diameter 1600 and catheter electrode 1414 spacing may be developed to provide a targeted range of energy density to tissue, as well as to provide sufficient electroporation coverage for different human anatomic geometries. In general, a sufficient number of electrodes 1414 with appropriate lengths 1604 are desired to provide substantially even and continuous coverage around the circumference of variable diameter loop 1500, while still allowing enough flexibility to allow variable diameter loop 1500 to expand and contract to vary diameter 1600 to the desired extremes. As mentioned above, length 1604 of catheter electrodes 141 may be varied. Increasing length 1604 of catheter electrodes 1414 may increase coverage of electrodes 1414 around the circumference of loop 1500 while also decreasing current density (by increasing the surface area) on electrodes 1414, which may help prevent arcing during electroporation operations. Increasing length 1604 too much, however, may prevent variable diameter loop 1500 from forming a smooth circular shape and may limit the closed diameter 1600 of variable diameter loop 1500. Additionally, too great a length 1604 may increase the surface area of catheter electrodes 1414 to a point that the current density applied to catheter electrodes 1414 by a power source is below the minimum current density needed for successful therapy. Conversely, decreasing length 1604 decreases the surface area, thereby increasing the current density (assuming no other system changes) on catheter electrodes 1414. As discussed above, greater current densities may lead to increased risk of arcing during electroporation, and may result in larger additional system resistances needing to be added to prevent electroporation. Moreover, in order to get a desired, even coverage about the circumference of variable diameter loop 1500, more catheter electrodes 1414 may be needed if length 1604 is decreased. Increasing the number of catheter electrodes 1414 on variable diameter loop 1500 may prevent variable diameter loop 1500 from being able to be contracted to a desired minimum diameter 1600.

Figure 17:
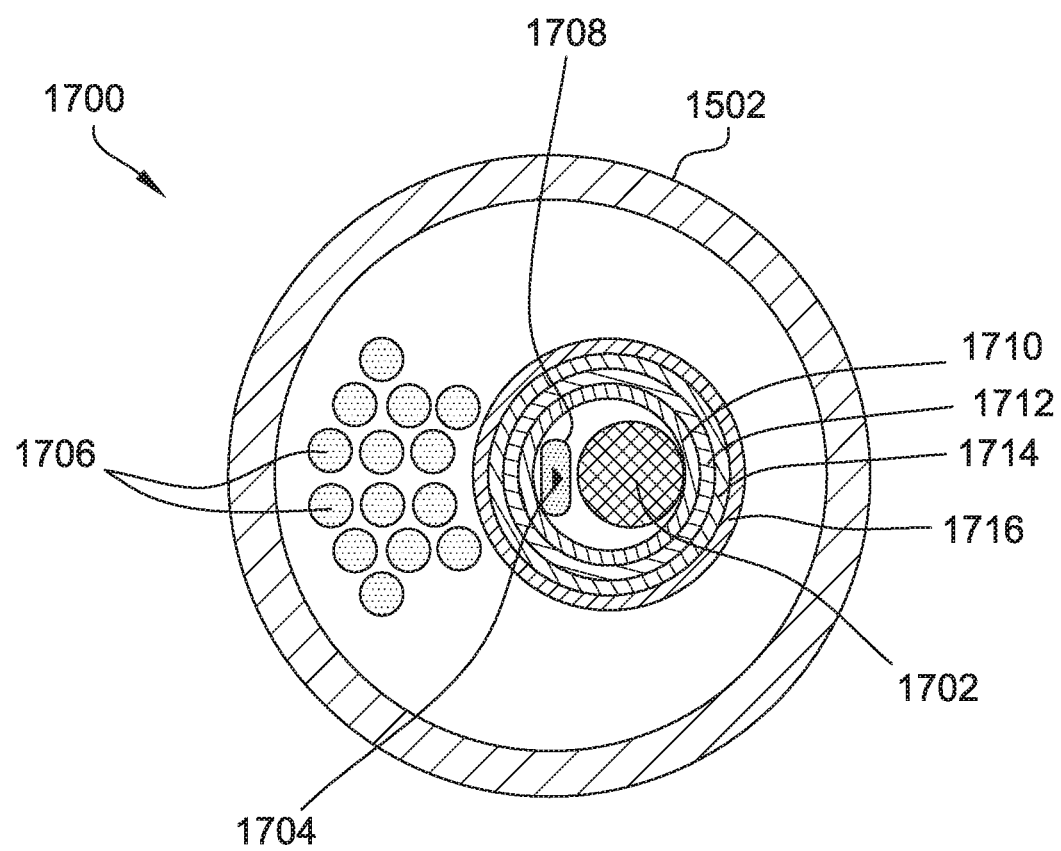
FIG. 17 is a cross-sectional view of a portion of the distal loop subassembly of FIG. 15 taken along the lone A-A.

FIG. 17 is a cross-section 1700 of variable diameter loop 1500 taken along the line A-A shown in FIG. 16. Cross-section 1700 includes a shape memory wire 1702, a pull wire 1704, electrode wires 1706, and tubing 1708, 1710, 1712, 1714, and 1716.

Shape memory wire 1702 is pre-shaped to a loop configuration at a particular diameter 1600 to shape variable diameter loop 1500 into its circular shape of the expanded diameter 1600. After a change in shape of variable diameter loop 1500, such as a change in diameter 1600 or a straightening for insertion into a patient's body, shape memory wire 1702 will substantially return variable diameter loop 1500 to its initial shape and diameter 1600. In the example embodiment, shape memory wire 1702 is a nitinol wire. In other embodiments, shape memory wire 1702 may be any other suitable shape memory alloy.

Pull wire 1704 is configured to permit an operator to vary diameter 1600 of variable diameter loop 1500 by moving a proximal end (not shown) of pull wire 1704 toward or away from proximal end 1410. Pull wire 1704 is surrounded by tubing 1708. Tubing 1708 is a polyethylene terephthalate (PET) shrink tubing. In other embodiments, tubing 1708 may be any other suitable tubing for insulating and protecting pull wire 1708.

Electrode wires 1706 carry electrical current from a power source coupled to connector 1408 to catheter electrodes 1414. Electrode wires 1706 are any suitable size and material sufficient to carry the voltage and current required for electroporation, as described herein. Each electrode wire 1706 is connected to a different catheter electrode 1414. Electrode wires 1706 are isolated from one another and are not electrically connected to each other within catheter 1400. In other embodiments, electrode wires 1706 may be connected together, for example in parallel, within variable diameter catheter 1400.

Shape memory wire 1702 and pull wire 1704 are separated from and electrically insulated from electrode wires 1706 by tubing 1710, 1712, 1714, and 1716. In the example embodiment, tubing 1710 is a polytetrafluoroethylene (PTFE) tubing, tubing 1712 is a polyimide tubing, and tubing 1714 and 1716 are PET shrink tubing.

Hoop catheter 1400 may further incorporate additional insulation materials to accommodate high voltages and currents. For instance, hoop catheter 1400 may include an insulator, such as wire sheathing (not shown), that surrounds each electrode wire 1706. Such a wire sheathing may, for example, have a thickness of 0.0015 inches. Similarly, hoop catheter 1400 may include insulation material (not shown) that is packed or bundled around electrode wires 1706 to insulate electrode wires 1706 from one another and/or from other components of hoop catheter 1400.

Figure 18:
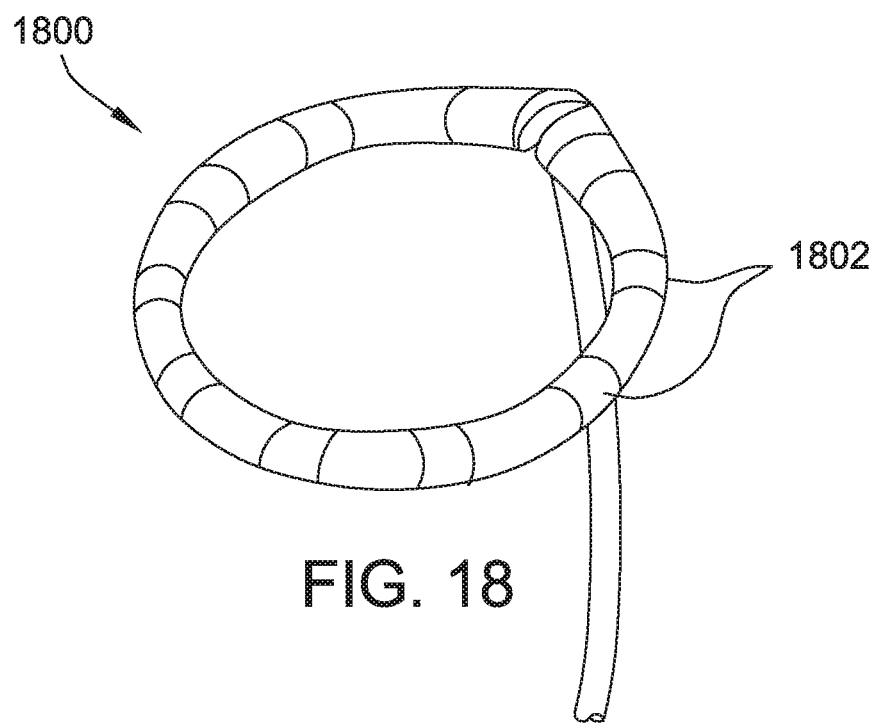
FIG. 18 is another example embodiment of a variable diameter, high output hoop catheter.
Figure 19:
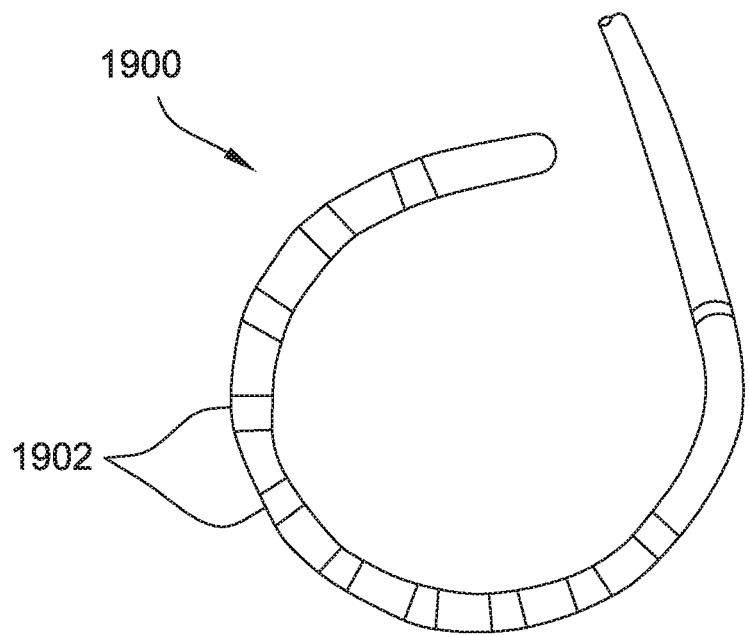
FIG. 19 is another example embodiment of a variable diameter, high output hoop catheter.
Figure 20:
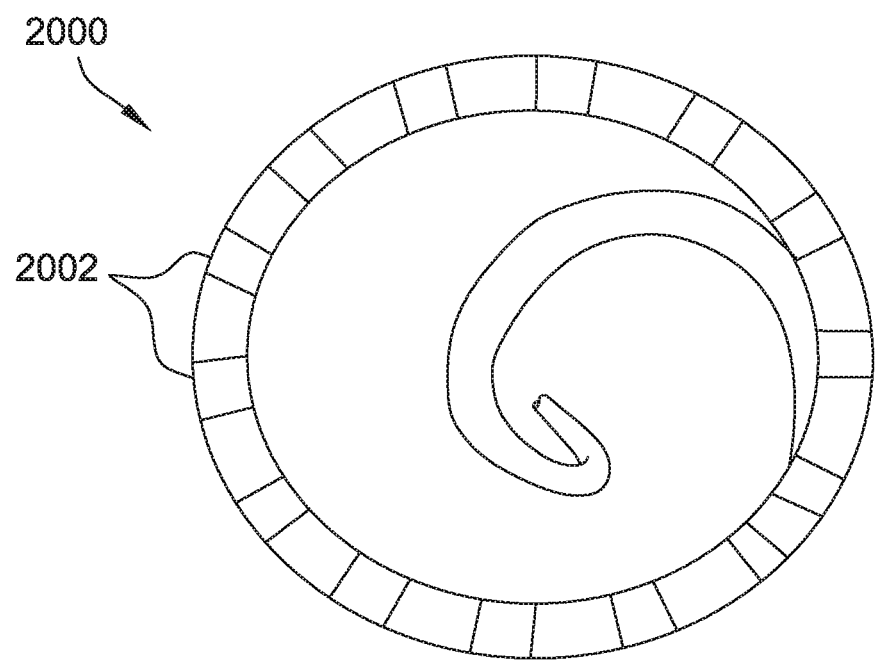
FIG. 20 is another example embodiment of a variable diameter, high output hoop catheter.

FIGS. 18-20 illustrate several alternative catheters usable, in some embodiments, as catheter 14.

For example, with attention to FIG. 18, a perspective view of a high output hoop catheter 1800 is shown. In the example embodiment, hoop catheter 1800 is a fixed diameter catheter (rather than a variable diameter catheter) having an fixed diameter of 20 mm. Catheter 1800 includes ten catheter electrodes 1802, each having a length 1804 of approximately 2 mm. Hoop catheter 1800 may be used with a Bi-D (Safire) handle and/or a Matrix proximal shaft. Hoop catheter 1800 has a circumferential loop/primary shaft orientation and a full circumferential shape in an open loop configuration.

Similarly, FIG. 19 is a perspective view of a high output hoop catheter 1900. In the example embodiment, hoop catheter 1900 is a variable diameter catheter configured for expansion and contraction. Catheter 1900 has an open loop diameter of 35 mm and a closed loop diameter of 15 mm. Catheter 1900 includes ten catheter electrodes 1902, each having a length of approximately 2 mm. Hoop catheter 1900 may be used with a Uni-D handle and a Matrix proximal shaft. Hoop catheter 1900 has a circumferential loop/primary shaft orientation and a C-shape in an open loop configuration.

FIG. 20 is a perspective view of a high output hoop catheter 2000. In the example embodiment, hoop catheter 2000 is a variable diameter catheter configured for expansion and contraction. Catheter 2000 has an open loop diameter of 27 mm and a closed loop diameter of 15 mm. Catheter 2000 includes fourteen catheter electrodes 2002, each having a length of approximately 2 mm. Hoop catheter 2000 may be used with a Uni-D (modified) handle and an MTC proximal shaft. Hoop catheter 2000 has a center loop/primary shaft orientation and a full circumferential shape in an open loop configuration.

Figure 21:
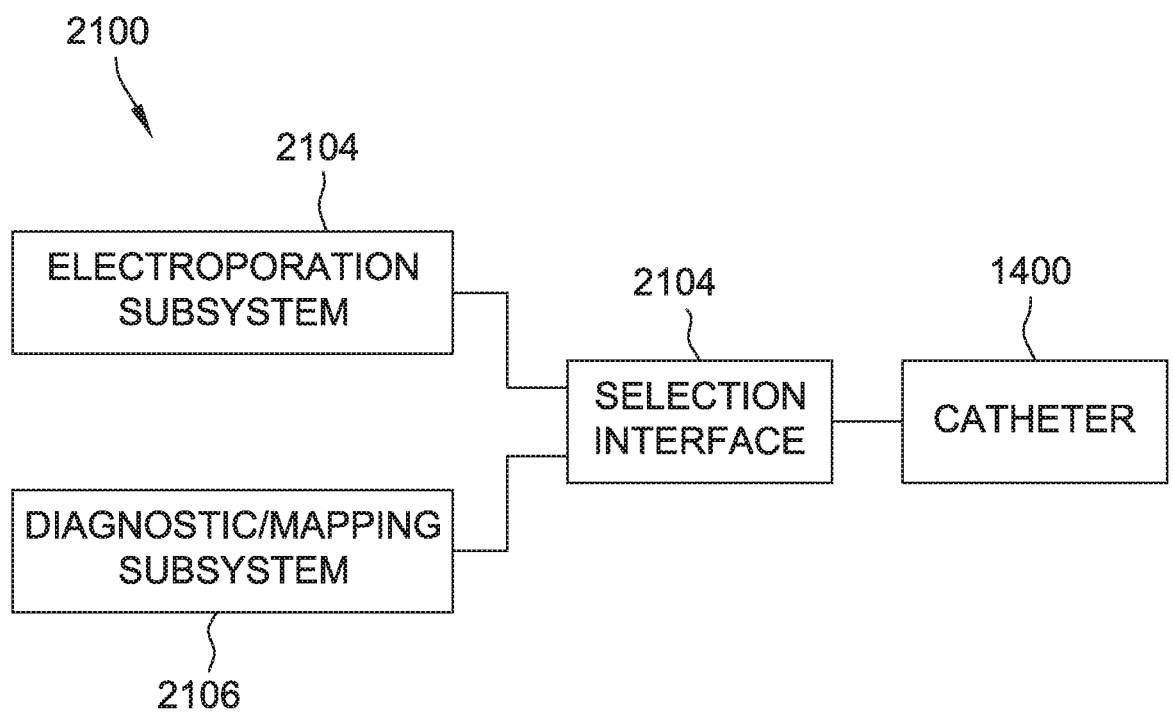
FIG. 21 is a block diagram of an example diagnostic and treatment system using a single catheter for diagnostic procedures and electroporation.

FIG. 21 is a simplified block diagram of another example system 2100 for electroporation therapy using catheter 1400. Except as otherwise described herein, system 2100 may be identical to or substantially similar to system 10. Unlike system 10, system 2100 includes a selection interface 2102 coupled between catheter 1400, an electroporation subsystem 2104, and a diagnostic or mapping subsystem 2106. Thus, system 2100 may include any element or component shown with respect to system 10. However, for purposes of illustration, system 2100 is shown in simplified format. Electroporation subsystem 2204 may include electroporation generator 26, and diagnostic/mapping subsystem 2106 may be identical to or substantially similar to localization and navigation system 30. In other embodiments, electroporation generator 2104 and diagnostic/mapping subsystem 2106 may be any two suitable subsystems for use with catheter 1400.

Selection interface 2102 is operable to select which of electroporation generator 2104 and diagnostic/mapping subsystem 2106 is coupled to catheter 1400, and more specifically, the catheter electrodes 1414 (not shown in FIG. 21). Thus, for example, an operator of system 2100 may insert the appropriate portion of catheter 1400 into a patient while coupled by selection interface 2102 to diagnostic/mapping subsystem 2106 to navigate catheter to a desired electroporation site and/or to map a portion of the patient. Once the catheter is suitably positioned, the same catheter 1400 may be coupled to electroporation subsystem 2104 by the operator making such a selection using selection interface 2102, and electroporation may proceed as described herein. Switching between electroporation subsystem 2104 and diagnostic/mapping subsystem 2106 may be accomplished by any suitable mechanical, electrical or electro-mechanical switches (not shown) within selection interface 2102.

Selection interface 2102 also facilitates selection of which catheter electrodes 1414 are coupled to the selected electroporation subsystem 2104 or diagnostic/mapping subsystem 2106, and in what electrical configuration. Switching between electrodes 1414 and electrical configuration of electrodes may be accomplished by any suitable mechanical, electrical or electro-mechanical switches (not shown) within selection interface 2102. For example, when connected to diagnostic/mapping subsystem 2106, each electrode 1414 (or a group of less than all electrodes) may be separately connected to diagnostic/mapping subsystem 2106 to allow each electrode to be utilized by diagnostic/mapping subsystem 2106 independent of all other electrodes 1414. During electroporation, however, it may be desirable to connect all electrodes 1414 in parallel to receive the same electroporation energy from electroporation subsystem 2104. Thus, when selection interface 2102 connects catheter 1400 to electroporation subsystem 1400, it connects all of catheters 1414 to electroporation subsystem 2104 in parallel. In other embodiments, other electrical configurations and combinations of electrical configurations may be used. For example, selection interface may be used to connect a group of less than all electrodes 1414 in parallel, but not connect the group in parallel to any other electrodes 1414 or other groups of electrodes 1414.

In some embodiments, selection interface 2102 includes or is included in a variable impedance, such as variable impedance 27. Thus, selection interface 2102 may also be used to connect variable impedance 27 to electrodes 1414 when connected to electroporation subsystem 2104 and disconnect electrodes 1414 from variable impedance 27 when catheter 1400 is connected to diagnostic/mapping subsystem 2106. Moreover, selection interface 2102 may be used to independently couple a same or different impedance to each catheter electrode 1414 or subgroups of electrodes 1414. Thus, in some embodiments, particularly if electrodes 1414 are not connected to each other in parallel, the impedance may be controlled at an individual electrode 1414 level to control the current density on each electrode (or subgroup of electrodes 1414) In some embodiments, selection interface 2102 may connect and disconnect one or more catheter electrodes 1414 from electroporation subsystem 2104 during operation to achieve desirable electroporation patterns and/or electroporation results during operation.

As described herein, electroporation through catheter, such as a hoop catheter used in cardiac ablation procedures, can creates arcs. These arcs create shockwaves that may cause barotrauma (i.e., pressure wave damage to tissue). Accordingly, the systems and methods described above are directed to limiting or preventing such arcing.

In the event that arcing does occur, however, it would be desirable to alert a physician or other operator. As described herein, such arcs may coincide with a positive deflection in the calculated impedance between catheter electrodes and the shock return. Various methodologies and processes may be used to identify an arc based on the impedance trace signature. If an electrophysiologist/physician recognizes that electroporation arced in a patient, the physician can act to mitigate harm.

In one embodiment, an ablation system (such as system 10 (shown in FIG. 1)) is configured to alert a physician or other operator that an arc occurred during electroporation therapy, and that a pressure wave was inflicted on the treatment region. This knowledge may guide subsequent medical decisions to reduce harm to the patient. In one embodiment, the arc is identified based on impedance signature deflections.

Figure 22:
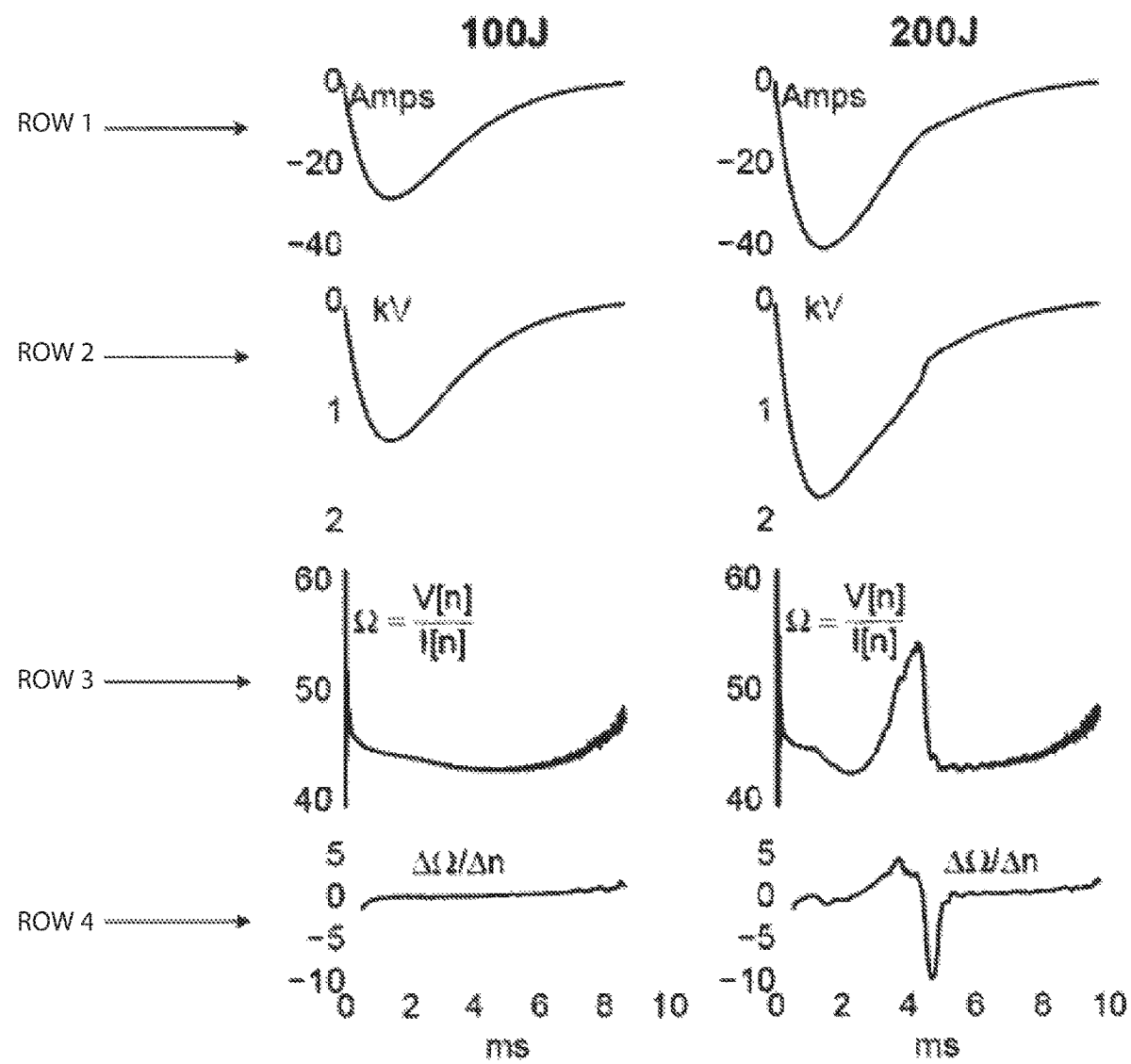
FIG. 22 shows graphs plotting data from an arcing shock and a non-arcing shock.

FIG. 22 shows data from an arcing shock and a non-arcing shock. The left column of FIG. 22 shows data from a non-arcing shock, and the right column of FIG. 22 shows data from an arcing shock through the same catheter. In one example, the calculated impedance is about 45 ohms in both cases. All arcs generally exhibit a large positive deflection as shown at 4 ms in the 200J shock impedance trace. The bottom trace (row 4) shows the derivative of the impedance to demonstrate one embodiment of an identification algorithm.

As shown in FIG. 22, impedance traces (row 3) of non-arcing shocks are more flat, as shown in the first column where 100 Joules of energy is applied, while those of arcing shocks exhibit a large deflection, as shown in the second column where 200 Joules of energy is applied.

In the exemplary embodiments, identification of arcs in accordance with the disclosure include, but are not limited to, thresholding the impedance value (with electrode impedance prior to shock subtracted out). Another example involves thresholding the derivative (see row 4 of FIG. 22). Another example involves combining the derivative threshold and the impedance threshold. Still another example involves detecting the larger impedance integral compared to that expected without arc (with electrode impedance prior to shock subtracted out). Yet another example involves thresholding the second derivative of impedance. Additionally, methodologies that identify R-waves on the surface ECG (such as Pan-Tompkins) could be modified to detect arc in some embodiments.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method of controlling an electroporation system including a direct current (DC) energy source, a return electrode connected to the DC energy source, and a catheter connected to the DC energy source, the catheter having at least one catheter electrode, the method comprising:
   positioning the return electrode near a target location within a body;
   positioning the catheter electrode within the body adjacent the target location within the body;
   determining a system impedance with the return electrode positioned near the target location and the catheter electrode positioned within the body;
   calculating a target impedance based on a combination of a current density threshold and a characteristic of the catheter; and
   adjusting the system impedance to calculated target impedance to limit arcing from the catheter electrode.

2. The method of claim 1, wherein adjusting the system impedance to the calculated target impedance comprises adjusting a system resistance to a target resistance.

3. The method of claim 2, wherein adjusting the system resistance comprises connecting at least one resistor to one of the catheter and the return electrode.

4. The method of claim 2, wherein adjusting the system resistance comprises removing at least one resistor connected to one of the catheter and the return electrode.

5. The method of claim 2, wherein the electroporation system includes an adjustable resistance connected to one of the catheter and the patch electrode, and adjusting the system resistance comprises varying the adjustable resistance.

6. The method of claim 1, wherein calculating the target impedance comprises calculating the target impedance based at least in part on one or more of a surface area of the catheter electrode, a shape of the catheter, a shape of the catheter electrode, a size of the catheter, a distance between the catheter electrode and an additional catheter electrode on the catheter, a time interval between pulses of energy output by the DC energy source, and a target electrical current density for the catheter electrode.

7. The method of claim 1, wherein determining the system impedance comprises:
   shorting the catheter electrode and an additional catheter electrode together; and
   outputting a known non-electroporation signal using the shorted catheter electrode and the additional catheter electrode.

8. A method of detecting arcing in an electroporation system including a direct current (DC) energy source, a return electrode connected to the DC energy source, and a catheter connected to the DC energy source, the catheter having at least one catheter electrode, the method comprising:
   positioning the return electrode near a target location within a body;
   positioning the catheter electrode within the body adjacent the target location within the body;
   monitoring a system impedance with the return electrode positioned near the target location and the catheter electrode positioned within the body;
   detecting a positive deflection in the system impedance, the positive deflection indicative of arcing, wherein the positive deflection is detected by monitoring one of i) the integral of the system impedance and ii) the second derivative of the system impedance; and
   generating an alert, based on the detection, the alert indicating that arcing has occurred.

* * * * *